US008956399B2

(12) United States Patent
Cam et al.

(10) Patent No.: US 8,956,399 B2
(45) Date of Patent: Feb. 17, 2015

(54) VASCULAR REMODELING DEVICE

(75) Inventors: Anh Cam, Carlsbad, CA (US); Michael Louis Losordo, San Juan Capistrano, CA (US); Jianlu Ma, Irvine, CA (US); Xiaoling Zhao, Irvine, CA (US)

(73) Assignee: Covidien LP, Mansfield, MA (US)

( * ) Notice: Subject to any disclaimer, the term of this patent is extended or adjusted under 35 U.S.C. 154(b) by 168 days.

(21) Appl. No.: 13/469,214

(22) Filed: May 11, 2012

(65) Prior Publication Data

US 2012/0290067 A1 Nov. 15, 2012

Related U.S. Application Data

(60) Provisional application No. 61/485,063, filed on May 11, 2011.

(51) Int. Cl.
*A61F 2/06* (2013.01)
*A61F 2/915* (2013.01)
*A61B 17/12* (2006.01)
*A61F 2/90* (2013.01)
*A61F 2/82* (2013.01)

(52) U.S. Cl.
CPC ........... *A61F 2/915* (2013.01); *A61B 17/12118* (2013.01); *A61F 2/90* (2013.01); *A61F 2002/823* (2013.01); *A61F 2240/001* (2013.01); *A61F 2250/0039* (2013.01); *A61B 17/12031* (2013.01); *A61B 17/1214* (2013.01); *A61B 17/12172* (2013.01)
USPC .......... 623/1.12; 623/1.15; 623/1.11; 623/1.2

(58) Field of Classification Search
CPC ................................ A61F 2002/821

USPC ............ 606/1, 108, 200; 623/1.11, 1.15, 1.3, 623/1.12, 1.35
See application file for complete search history.

(56) References Cited

U.S. PATENT DOCUMENTS

| 5,948,018 | A | * | 9/1999 | Dereume et al. | 623/1.12 |
| 5,980,554 | A | | 11/1999 | Lenker et al. | |
| 6,261,305 | B1 | | 7/2001 | Marotta et al. | |
| 6,706,062 | B2 | * | 3/2004 | Vardi et al. | 623/1.15 |
| 6,730,119 | B1 | * | 5/2004 | Smalling | 623/1.35 |
| 6,773,454 | B2 | * | 8/2004 | Wholey et al. | 623/1.15 |
| 7,220,275 | B2 | | 5/2007 | Davidson et al. | |

(Continued)

FOREIGN PATENT DOCUMENTS

| DE | 10 2007 012964 | 9/2008 |
| WO | WO 00/07524 | 2/2000 |

(Continued)

*Primary Examiner* — Tuan V Nguyen
*Assistant Examiner* — Chima Igboko
(74) *Attorney, Agent, or Firm* — Mark J. Kertz, Esq.

(57) ABSTRACT

Described herein are flexible implantable devices or stents that can conform to the shape of vessels of the neurovasculature. In some embodiments, the devices can direct blood flow within a vessel away from an aneurysm or limit blood flow to the aneurysm. In some embodiments, a vascular remodeling device includes a first section and a protruding section. During deployment, the device expands from a compressed configuration to an expanded configuration. The first section anchors the device in an afferent vessel and/or in an efferent vessel of a bifurcation and the protruding section is positioned in the junction of the bifurcation having an aneurysm and across the neck of the aneurysm or at least partially within the aneurysm.

15 Claims, 9 Drawing Sheets

(56) References Cited

U.S. PATENT DOCUMENTS

| | | | |
|---|---|---|---|
| 7,578,841 B2* | 8/2009 | Yadin et al. | 623/1.35 |
| 7,645,296 B2 | 1/2010 | Theron et al. | |
| 7,686,846 B2 | 3/2010 | Laborde et al. | |
| 7,744,643 B2 | 6/2010 | Hegg | |
| 7,842,081 B2 | 11/2010 | Yadin | |
| 7,942,925 B2 | 5/2011 | Yodfat et al. | |
| 8,419,782 B2* | 4/2013 | Bruszewski | 623/1.11 |
| 2002/0156516 A1* | 10/2002 | Vardi et al. | 623/1.11 |
| 2003/0139796 A1* | 7/2003 | Sequin et al. | 623/1.12 |
| 2004/0024441 A1* | 2/2004 | Bertolino et al. | 623/1.12 |
| 2004/0158311 A1* | 8/2004 | Berhow et al. | 623/1.15 |
| 2004/0172056 A1 | 9/2004 | Guterman et al. | |
| 2004/0215316 A1* | 10/2004 | Smalling | 623/1.11 |
| 2004/0260385 A1* | 12/2004 | Jones et al. | 623/1.12 |
| 2005/0060017 A1* | 3/2005 | Fischell et al. | 623/1.11 |
| 2005/0096726 A1* | 5/2005 | Sequin et al. | 623/1.12 |
| 2005/0177221 A1* | 8/2005 | Mustapha | 623/1.11 |
| 2006/0064151 A1* | 3/2006 | Guterman et al. | 623/1.3 |
| 2006/0100684 A1* | 5/2006 | Elliott | 623/1.2 |
| 2006/0190070 A1* | 8/2006 | Dieck et al. | 623/1.12 |
| 2007/0073376 A1* | 3/2007 | Krolik et al. | 623/1.11 |
| 2007/0073388 A1* | 3/2007 | Krolik et al. | 623/1.31 |
| 2007/0173921 A1* | 7/2007 | Wholey et al. | 623/1.13 |
| 2007/0198075 A1* | 8/2007 | Levy | 623/1.11 |
| 2007/0203559 A1* | 8/2007 | Freudenthal et al. | 623/1.3 |
| 2007/0203567 A1* | 8/2007 | Levy | 623/1.15 |
| 2007/0219610 A1 | 9/2007 | Israel | |
| 2007/0276468 A1 | 11/2007 | Holzer et al. | |
| 2008/0109063 A1* | 5/2008 | Hancock et al. | 623/1.12 |
| 2009/0132024 A1 | 5/2009 | Berkhoff | |
| 2009/0163993 A1* | 6/2009 | Chalekian et al. | 623/1.15 |
| 2009/0216307 A1* | 8/2009 | Kaufmann et al. | 623/1.3 |
| 2009/0299460 A1* | 12/2009 | Meyer et al. | 623/1.12 |
| 2010/0023105 A1* | 1/2010 | Levy et al. | 623/1.2 |
| 2011/0009941 A1 | 1/2011 | Grandfield | |
| 2011/0022149 A1 | 1/2011 | Cox et al. | |
| 2011/0184452 A1 | 7/2011 | Huynh et al. | |

FOREIGN PATENT DOCUMENTS

| | | |
|---|---|---|
| WO | WO 2005/011527 | 2/2005 |
| WO | WO-2008/042778 A2 | 4/2008 |
| WO | WO-2010/150208 A2 | 12/2010 |

* cited by examiner

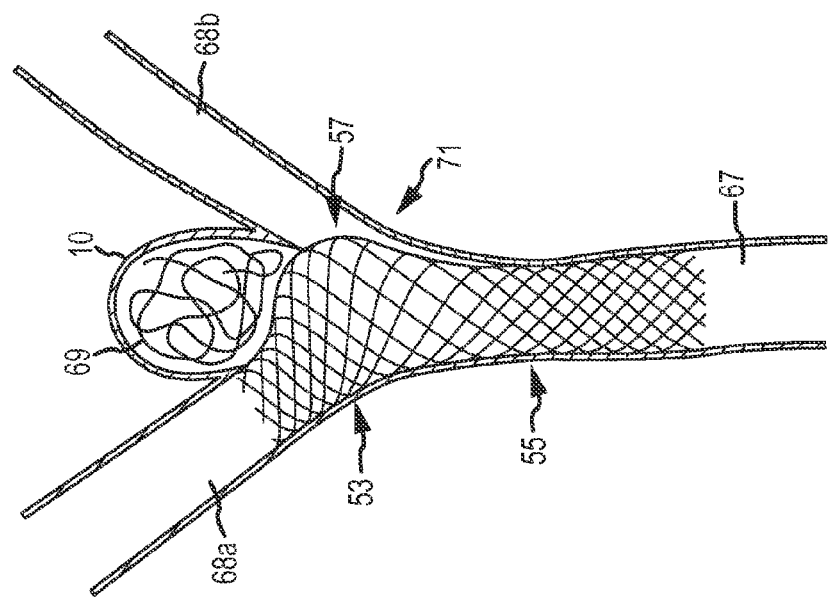
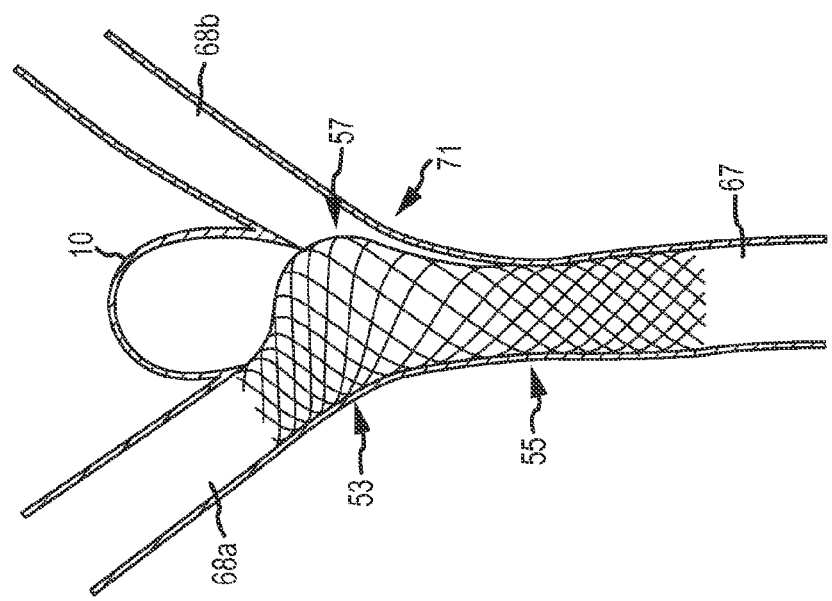

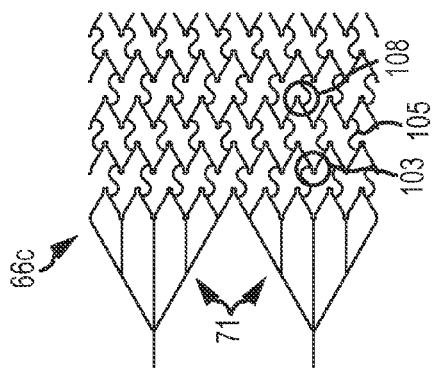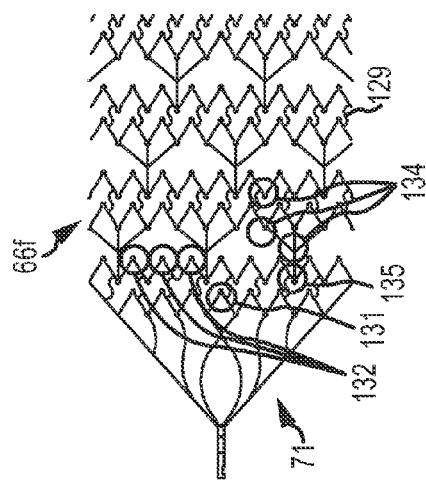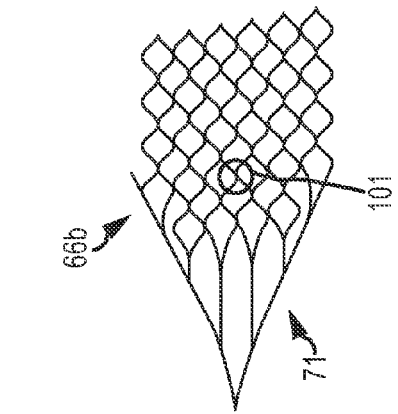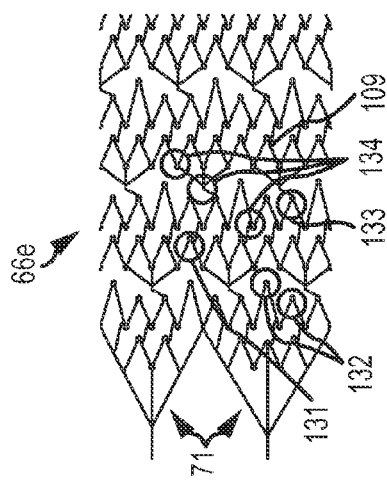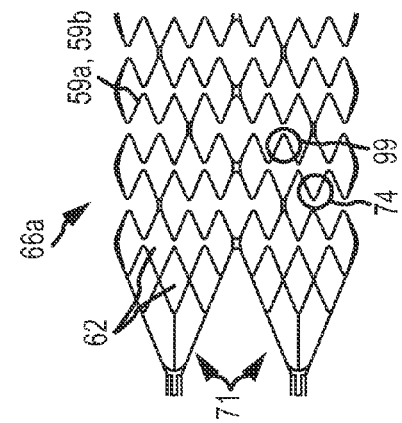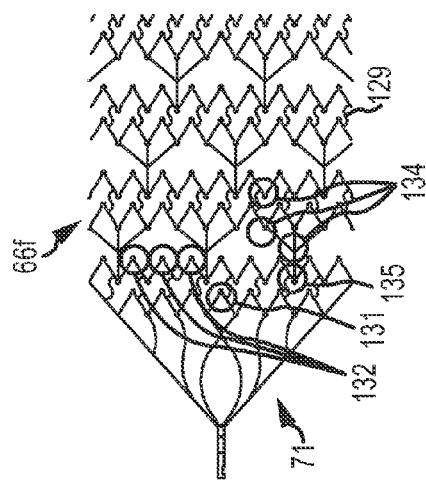

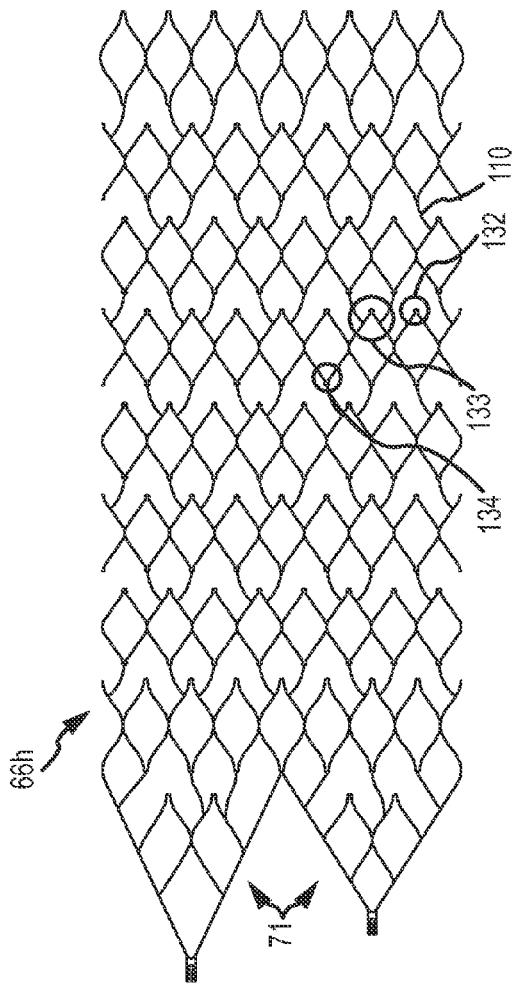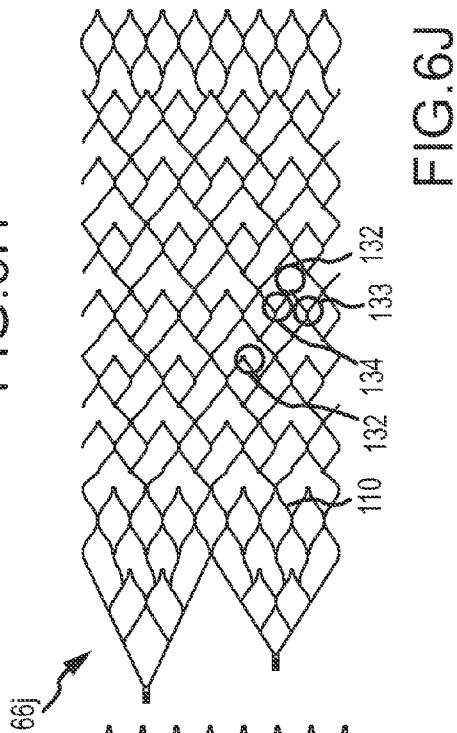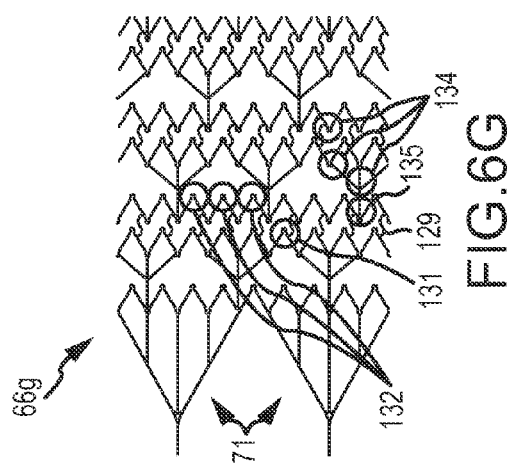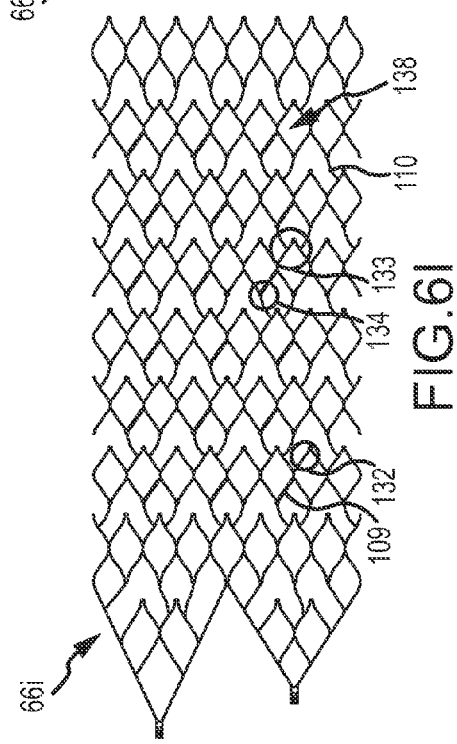

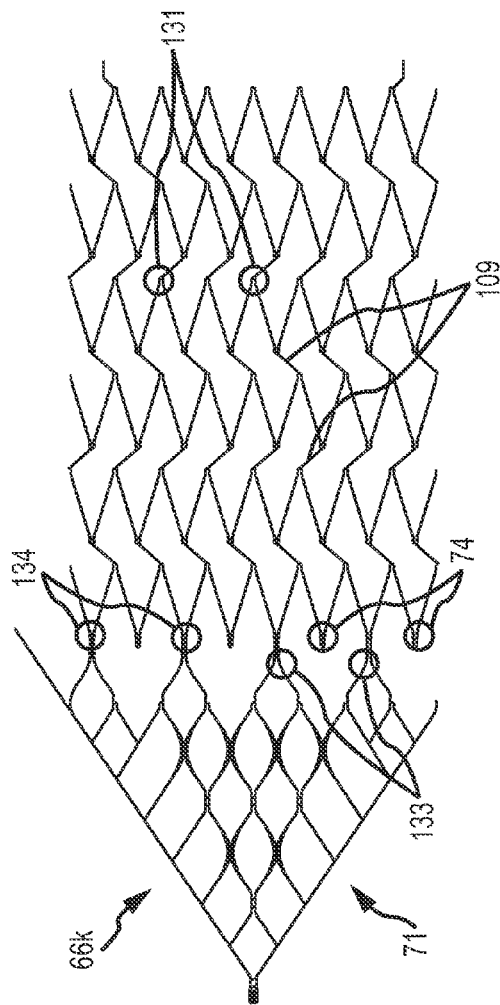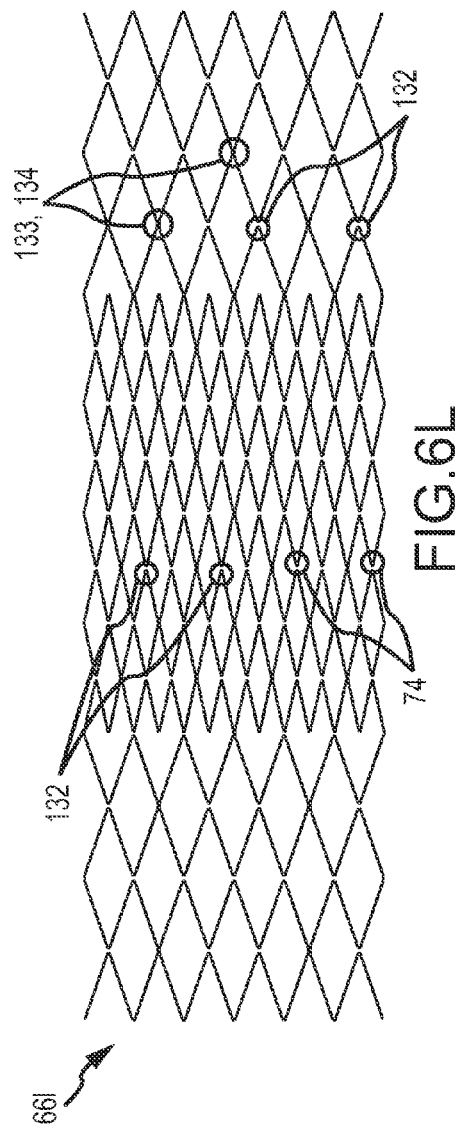

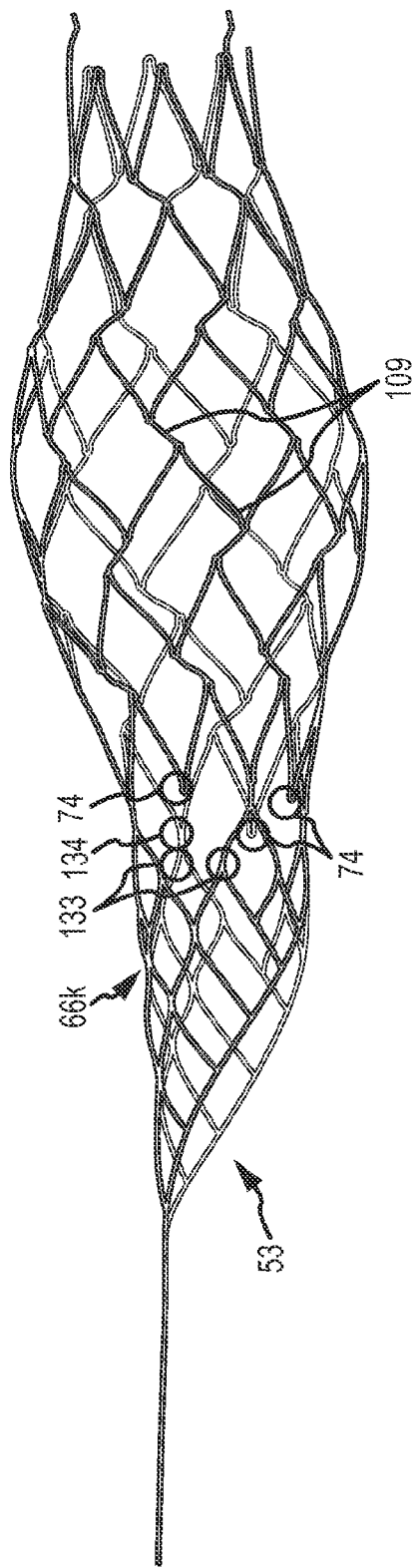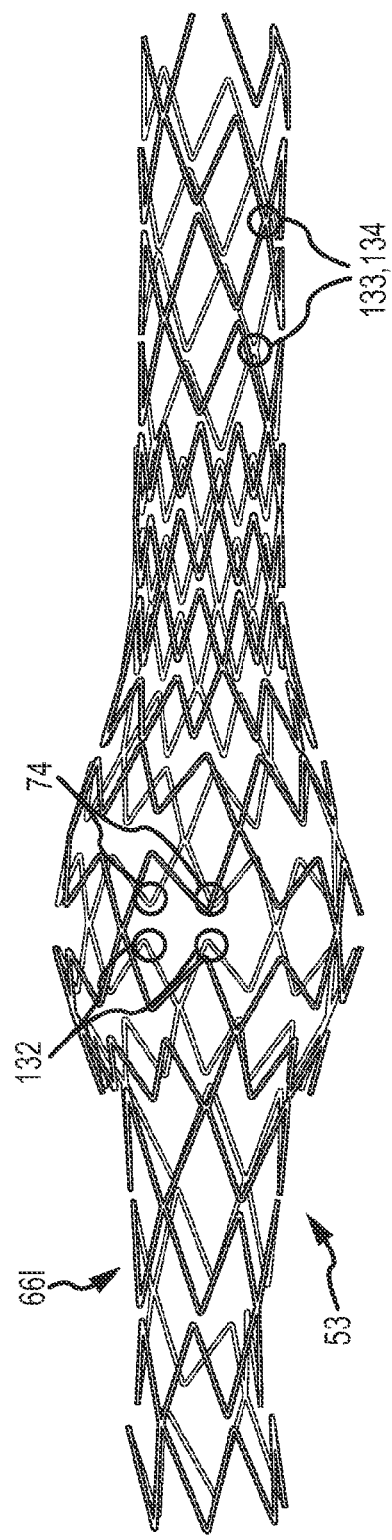

VASCULAR REMODELING DEVICE

CROSS-REFERENCE TO RELATED APPLICATIONS

The present application claims priority to U.S. Provisional Patent Application No. 61/485,063 entitled "Vascular Remodeling Device," and filed on May 11, 2011. The contents of the priority application are hereby incorporated by reference in their entirety.

FIELD OF THE INVENTION

The present application generally relates to implantable devices for use within a patient's body and, more particularly, relates to methods for implanting occluding devices, such as stents, in a patient's body and monitoring an occlusion.

BACKGROUND

Lumens in a patient's body can change in size, shape, and/or patency, and such changes can present complications or affect associated bodily functions. For example, the walls of the vasculature, particularly arterial walls, may develop a pathological dilatation, commonly called an aneurysm. Aneurysms are observed as a ballooning-out of the wall of an artery. This is a result of the vessel wall being weakened by disease, injury, or a congenital abnormality. Aneurysms have thin, weak walls and have a tendency to rupture and are often caused or made worse by high blood pressure. Aneurysms can be found in different parts of the body; the most common being abdominal aortic aneurysms (AAA) and the brain or cerebral aneurysms. The mere presence of an aneurysm is not always life-threatening, but an aneurysm can have serious health consequences such as a stroke if one should rupture in the brain. Additionally, a ruptured aneurysm can also result in death.

SUMMARY

In some embodiments, described herein are embodiments of a vascular stent that includes a proximal section having a first cross-sectional dimension and being configured to anchor in an afferent vessel of a bifurcation proximate to an aneurysm, the proximal section comprising a tubular shape that defines a proximal lumen; a distal section having a second cross-sectional dimension and being configured to be positioned in an efferent vessel of the bifurcation, the distal section comprising a tubular shape that defines a distal lumen; and a protruding section, between the proximal and distal sections, having a third cross-sectional dimension, the protruding section (i) being configured to abut an ostium of the aneurysm when the protruding section is positioned at the bifurcation, (ii) defining an intermediate lumen in fluid communication with the proximal and distal lumens, and (iii) having a strut pattern that is substantially the same as strut patterns of the proximal and distal sections. In some embodiments, the proximal, distal and protruding sections are expandable from a compressed configuration to an expanded configuration.

Some embodiments provide that the protruding section is configured to inhibit dislodgment of objects out of the aneurysm. In some embodiments, the strut patterns of the proximal, distal, and protruding sections define substantially similar cell sizes. In certain embodiments, cell sizes of the strut pattern in the protruding section are configured to allow perfusion of fluid to efferent vessels. In some embodiments, the proximal, distal, and protruding sections comprise nonuniform cross-sectional dimensions when the stent is unconstrained. Some embodiments provide that the protruding section comprises an irregular-shaped cross-section.

In some embodiments, the protruding section is expandable to a further expanded configuration, the further expanded configuration defining a fourth cross-sectional dimension greater than the third cross-sectional dimension. In some embodiments, the proximal, distal, and protruding sections comprise woven filaments. Some embodiments provide that at least one of the proximal, distal, and protruding sections is self-expandable. In some embodiments, at least one of the proximal and distal sections comprises a first material and the protruding section comprises a second material different from the first material.

In certain embodiments, the stent further includes (i) a first intermediate section, between the proximal and protruding sections, having a first taper, from the proximal section to the protruding section, and (ii) a second intermediate section, between the distal and protruding sections, having a second taper, from the distal section to the protruding section, the first taper having a different degree of tapering than the second taper. In some embodiments, the second taper has a steeper degree of tapering than does the first taper.

In some embodiments, the protruding section bulges radially outward along substantially an entire circumference of the device. In certain embodiments, a bulge of the protruding section provides a generally asymmetrical profile. Some embodiments provide at least a portion of the protruding section comprises a lower filament density than at least one of another portion of the protruding section, the proximal section, and the distal section.

Some methods described herein for treating an aneurysm at a junction of a bifurcation, having first and second efferent vessels, include advancing a catheter to the first efferent vessel of the bifurcation; advancing, relative to and within the catheter, a stent in a compressed configuration, the stent comprising (i) a proximal section having a first cross-sectional dimension and a tubular shape that defines a proximal lumen, (ii) a distal section having a second cross-sectional dimension and a tubular shape that defines a distal lumen; and (iii) a protruding section, between the proximal and distal sections, having a third cross-sectional dimension and defining an intermediate lumen in fluid communication with the proximal and distal lumens, the protruding section having a strut pattern that is substantially the same as struts patterns of the proximal and distal sections; expanding, to an expanded configuration, the proximal and distal sections to anchor the stent in the efferent and an afferent vessel; and expanding the protruding section at the bifurcation, such that the protruding section abuts an ostium of the aneurysm and inhibits dislodgment of objects out of the aneurysm. In some methods, after the expanding steps, the proximal, intermediate, and distal lumens provide a substantially unobstructed path for fluid flow from the afferent vessel to the first efferent vessel and the strut pattern of the protruding section permits fluid flow to the second efferent vessel.

In certain methods, at least one of the proximal, distal, and protruding sections self-expands. Some methods further include withdrawing the stent at least partially back into the catheter after a portion of the stent has been advanced out of the catheter.

Some methods further include inserting embolic material into the aneurysm. In some methods, embolic material is inserted into the aneurysm before sections of the stent are expanded. In certain methods, embolic material is inserted into the aneurysm after sections of the stent are expanded. In some methods, embolic material is inserted into the aneurysm through a wall of the stent defined by the strut pattern of the protruding section.

Some methods described manufacturing of a vascular device, and some methods include forming a substantially tubular stent having a substantially similar strut pattern throughout the stent; shape setting the stent to form (i) a proximal section having a first cross-sectional dimension and a proximal lumen and (ii) a distal section having a second cross-sectional dimension and a distal lumen; and shape setting the stent to form a protruding section, between the proximal and distal sections, having a third cross-sectional dimension greater than the first and second cross-sectional dimensions, wherein the proximal section is configured to anchor in an afferent vessel of a bifurcation comprising an aneurysm, the protruding section is configured to be positioned at the bifurcation and to act as a scaffolding to inhibit dislodgment of objects out of the aneurysm by abutting an ostium of the aneurysm, and the distal section is configured to be positioned in an efferent vessel of the bifurcation. In some methods, the proximal, intermediate, and distal lumens are configured to provide a substantially unobstructed fluid flow path from the afferent vessel to the efferent vessel.

In some methods, the forming includes cutting a tube. In some methods, the forming includes cutting a sheet and shape setting the sheet into a substantially tubular shape. In some methods, the forming includes weaving a plurality of wires and shape setting the plurality of wires into a substantially tubular shape.

In certain methods, the strut pattern defines substantially similar cell sizes. Certain methods further include shape setting (i) a first intermediate section, between the proximal and protruding sections, having a first taper, from the proximal section to the protruding section, and (ii) a second intermediate section, between the distal and protruding sections, having a second taper, from the distal section to the protruding section, the first taper having a different degree of tapering than the second taper. In some methods, the second tapered portion, is formed to have a steeper degree of tapering than does the first tapered portion.

In another aspect of the disclosure, a method of treating an aneurysm at a junction of a bifurcation having an afferent vessel and efferent vessels is disclosed. The aneurysm may have a neck and a fundus. The method may include advancing a catheter to a first efferent vessel of the bifurcation. The method may also include advancing, relative to and within the catheter, a vascular device in a compressed configuration. The device may include a first section configured to anchor in at least one of the afferent vessel and the first efferent vessel, and a protruding section coupled to the first section and being configured to inhibit protrusion of objects out of the aneurysm. The method may further include allowing the vascular device to expand to an expanded configuration as the vascular device is advanced out of the catheter, and allowing the protruding section to expand to a further expanded configuration at the junction of the bifurcation. The first section may have a first transverse dimension in the expanded configuration and the protruding section may have a second transverse dimension in the further expanded configuration. The second transverse dimension may be greater than the first transverse dimension.

In some embodiments, the method may further releasing the vascular device from the catheter. Releasing the vascular device from the catheter may include mechanical detachment, electrolytic detachment, and/or chemical detachment.

In some embodiments described herein, the protruding section may be configured to reduce an effective width of a neck of the aneurysm. In some embodiments, the protruding section may bulge radially outward along substantially an entire circumference of the device. In other embodiments, the protruding section may bulge radially outward along a portion of a circumference of the device. In yet other embodiments, the bulge of the protruding section provides a generally symmetrical profile. In yet other embodiments, the bulge of the protruding section provides a generally asymmetrical profile. In yet other embodiments, the protruding section bulges outwardly towards a line or a point. In further embodiments, the protruding section bulges outwardly in a substantially rounded manner.

In some aspects of the disclosure, a method of manufacturing a vascular device is disclosed. The method may include forming a substantially tubular device, and shape setting the tubular device to form a first section having a first transverse dimension. The method may further include shape setting the tubular device to form a protruding section having a second transverse dimension. The second transverse dimension may be greater than the first transverse dimension. The first section may be configured to anchor in a vessel of a bifurcation that has an aneurysm. The protruding section may be configured to act as a scaffolding to inhibit protrusion of objects out of the aneurysm. At least one of the first section and the protruding section may be configured to allow perfusion of fluid to efferent vessels.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

FIG. 4A illustrates an exemplary vascular remodeling device as deployed at a bifurcation having efferent vessels and an aneurysm, according to one or more embodiments disclosed.

FIG. 4B illustrates the exemplary vascular remodeling device of FIG. 4A where the protruding section acts as scaffolding, according to one or more embodiments disclosed.

FIGS. 6A, 6B, 6C, 6D, 6E, 6F, 6G, 6H, 6I, 6J, 6K, 6L illustrate exemplary cell patterns that may be employed on the various vascular remodeling devices described herein, according to one or more embodiments disclosed.

FIGS. 7A and 7B illustrate exemplary vascular remodeling devices using various cell patterns, according to one or more embodiments disclosed.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

Figure 1B:
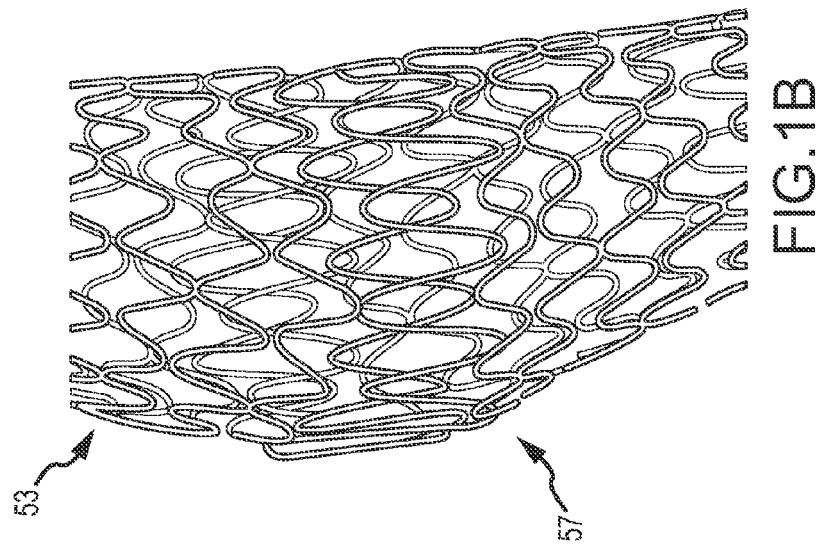
FIG. 1B illustrates an enlarged view of the vascular remodeling device shown in FIG. 1A, according to one or more embodiments.
Figure 1A:
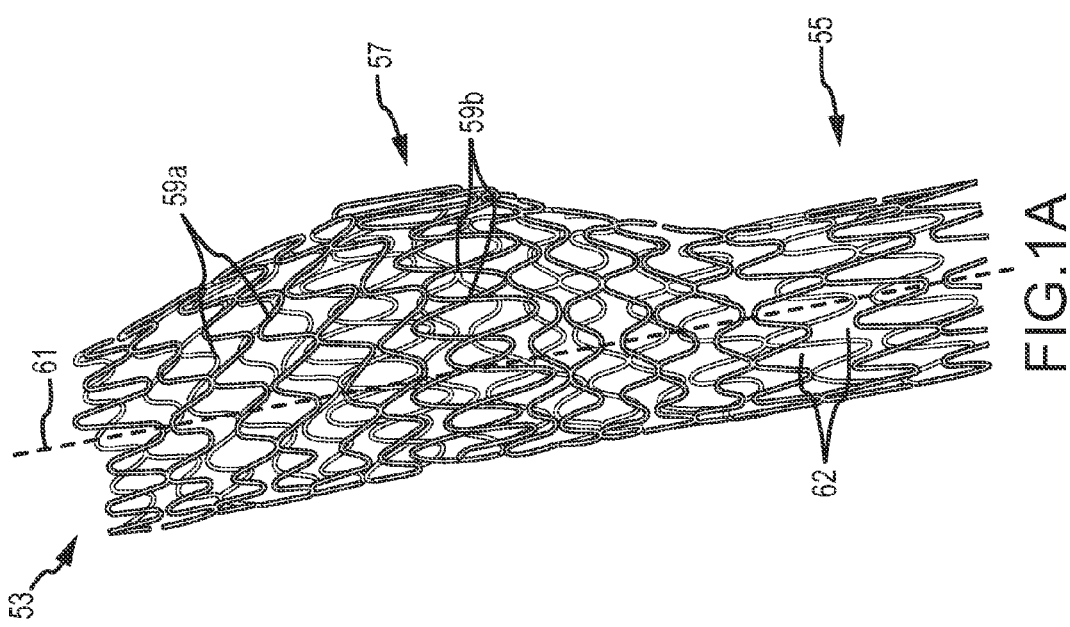
FIG. 1A illustrates an exemplary vascular remodeling device, according to one or more embodiments disclosed.

Referring now to FIGS. 1A and 1B, illustrated is an exemplary vascular device 53, according to one or more embodiments of the disclosure. The vascular device 53 may be characterized as an occluding device, such as a vascular occluding device, or a stent and may be used generally in vascular remodeling applications. The device 53 is movable between a compressed configuration and an expanded configuration and includes a first section 55 and a second, or protruding section 57. The device 53 may comprise one or more additional sections, such as a third section adjacent to the protruding section 57 on a side thereof opposite the first section 55. A third section may have characteristics similar or equal to the first section 55, as disclosed herein. In some embodiments, the device 53 is more compliant than the vasculature in which it is deployed such that it may be somewhat misshapen once deployed in the vasculature or otherwise conform to the general shape of the vasculature, and that certain protruding shapes described herein are achievable when the device 53 is an expanded configuration with no restriction.

The first section 55 may be characterized as an "in-vessel section," "main body," "stem," "tubular portion," or "anchoring section." The second or protruding section 57 may be characterized as a "scaffolding section," "bulging or pregnant section," or "extruded section." In one or more embodiments, the device 53 may be delivered via an elongate body (not shown), such as a catheter or microcatheter, into a bifurcation in order to support an aneurysm filling device with minimal interruption of blood flow in afferent and/or efferent vessels. In some embodiments, the device 53 may be retrievable and/or repositionable, without departing from the scope of the disclosure.

The device 53 may have a round (e.g., circular, elliptical, or ovoid) cross section. In some embodiments, the device 53 includes filaments 59a having a substantially rectangular or flat cross section (e.g., embodiments in which the device 53 comprises ribbons or uncut portions of a metallic tube or sheet). In some embodiments, the device 53 includes filaments 59a having a substantially round (e.g., circular, elliptical, ovoid) cross section. The filaments 59a may be coupled at the proximal end of the device 53, at the distal end of the device 53, or at both the proximal and distal ends. In some embodiments, the filaments 59a are configured to form a mesh, such as a criss-cross or braided mesh. To form the mesh-like configuration, the filaments 59a may be attached, welded, glued, adhered, mechanically crimped, mechanically swaged, braided, woven, physical vapor deposited, chemical vapor deposited, combinations thereof, or the like. In some embodiments, a tube or sheet of desired material may be cut, such as laser cut or mechanically-cut, to form filaments 59a arranged in a particular configuration. Other filament mesh patterns of the device 53 are also possible, such as those described below with respect to FIGS. 6A-6L.

In some embodiments, the first section 55 may extend longitudinally from one side of the protruding section 57. In other embodiments, however, the first section 55 may longitudinally extend from both sides of the protruding section 57, such that the protruding section 57 is interposed between the ends of the first section 55. In certain embodiments, the first section 55 may be configured to anchor the device 53 within a patient's vasculature. For example, when the device 53 is placed at a bifurcation, the first section 55 may anchor the device 53 in an afferent vessel (e.g., as generally shown in FIGS. 4A and 4B). In other embodiments, the first section 55 may also or alternatively anchor the device 53 in an efferent vessel. In yet other embodiments, the first section 55 may anchor the device 53 in a combination of afferent and efferent vessels.

In one or more embodiments, the first section 55 may longitudinally extend from both sides of the protruding section 57, but may only anchor on one side of the protruding section 57 (e.g., in either the afferent or efferent vessels). As can be appreciated, the first section 55 longitudinally extending from both sides of the protruding section 57 may ensure that the protruding section 57 remains properly positioned and anchored at the treatment site. The first section 55 may also facilitate delivery, positioning, retrieval, and/or repositioning of the device 53. The first section 55 may be flexible and yet have enough radial force to anchor or maintain the position of the device 53 at a bifurcation after deployment such that it inhibits or prevents undesirable longitudinal migration of the device 53.

FIG. 1A depicts the device 53 in its expanded configuration and having a variable transverse dimension along its longitudinal axis 61. Specifically, the first section 55 may exhibit a first transverse dimension and the protruding section 57 may exhibit a second, larger transverse dimension. As illustrated, the second or protruding section 57 bulges or otherwise protrudes radially outward from the first section 55, thereby achieving the second transverse dimension. The respective transverse dimensions may correspond to the overall width or diameter of the device 53 over the respective sections 55, 57 at a given point along the longitudinal axis 61.

The device 53 may assume its compressed configuration while in a catheter or other type of elongate delivery device. Upon deployment from the catheter, the device 53 may be configured to automatically expand from the compressed configuration to its expanded configuration. The protruding section 57 may be configured to expand beyond the expanded configuration of the device 53 to a "further expanded configuration," thereby generating or otherwise providing the bulging area in the device 53. Accordingly, the device 53 may exhibit a non-uniform cross-sectional dimension is its expanded or relaxed state. In at least one embodiment, the protruding section 57 may be adapted to expand from the compressed configuration to the further expanded configuration without the device 53 first transitioning through the expanded configuration.

The protruding section 57 may be made of the same material and pattern as the first portion 52, but may be shape-set or otherwise configured to bulge radially outward and generate an increased cross-sectional dimension or diameter as compared with the other portions of the device 53. In some embodiments, the protruding section 57 may bulge radially outward along a portion of its circumference (e.g., along half of the circumference, along a third of the circumference, etc.). For example, in its fully expanded configuration, the device 53 may be substantially co-cylindrical with the first section 55 along one angular portion of the circumference of the protruding section 57 and non-co-cylidrical (e.g., due to the bulging of the protruding section 57) along another angular portion of the circumference. In other embodiments, the protruding section 57 may bulge radially outward about the entire circumference thereof.

In some embodiments, the protruding section 57 may bulge radially outward in a direction generally perpendicular to the longitudinal axis 61 of the device 53. In other embodiments, the protruding section 57 may bulge radially outward in a direction other than generally perpendicular to the longitudinal axis 61. In some embodiments, the protruding section 57 may be formed of a different pattern and/or material than the first section 55. The diameter or circumference of the protruding section 57 may increase along an axial length of the protruding section 57 and then decrease along the remainder of the axial length of the protruding section 57.

FIG. 1B illustrates an enlarged view of the protruding section 57. The bulging or distended portion of the protruding section 57 may resemble an ellipsoid protruding from the device 53. Other shapes are also possible such as, but not limited to, a pyramid, a prism, a sphere, a cone, a toroid, combinations thereof, and the like, without departing from the scope of the disclosure.

In some embodiments, the protruding section 57 may be deployed within the patient's vasculature such that it extends across at least a portion of the neck of an aneurysm, thereby reducing the effective width of the neck. In other embodiments, the protruding section 57 may be configured to extend across the entire neck of the aneurysm. In one or more embodiments, the protruding section 57 may extend partially within the aneurysm, and in other embodiments, the protruding section 57 may extend past the aneurysm and into one or both of the afferent and efferent vessels. In operation, the protruding section 57 may serve as a scaffolding section and may allow for the safe and controlled placement of one or more embolization coils within the fundus of the aneurysm. In some embodiments, the protruding section 57 allows perfusion to efferent vessels.

The device 53 may include a plurality of perforations or cells 62 defined by the mutual engagement of the filaments 59a. In some embodiments, the cells 62 have a size of about 1 mm×about 1.2 mm. Other cell sizes and relative dimensions, such as cells 62 having equal side lengths, are also possible. Moreover, other cell shapes, such as quadrilateral, parallelogram, rhombus, rectangle, square, hexagon, etc., are also possible without departing from the scope of the disclosure.

In certain embodiments, a percentage of at least a portion of the protruding section 57 formed by the filaments 59a is greater than about 3%. In certain embodiments, a percentage of at least a portion of the protruding section 57 formed by the filaments 59a is less than about 50%. In certain embodiments, a percentage of at least a portion of the protruding section 57 covered by the cells 62 is less than about 97%. In certain embodiments, a percentage of at least a portion of the protruding section 57 covered by the cells 62 is greater than about 50%. In certain embodiments, a percentage of at least a portion of the protruding section 57 formed by the filaments 59a is between about 3% and about 25%. In certain embodiments, a percentage of at least a portion of the protruding section 57 covered by the cells 62 is between about 75% and about 97%. As will be appreciated, however, other porosities and densities of the protruding section 57 are also possible. In some embodiments, a lower porosity may enable the protruding section 57 to provide more scaffolding support for embolic material in the aneurysm.

In one or more embodiments, a portion of the protruding section 57 may include additional filaments 59b configured to increase filament density and, given the appropriate filament density, may enhance the ability of the protruding section 57 to act as a scaffolding that inhibits the herniation or prolapse of objects (e.g., embolic material, thrombi, etc.) from the neck of the aneurysm. In certain embodiments, at least a portion of the protruding section 57 is substantially devoid of a mesh or additional filaments 59b.

In some embodiments, the additional filaments 59b may be formed separately and then attached to the protruding section 57 as a collar or a patch. The additional filaments 59b may be attached to the protruding section 57 by various means such as, but not limited to, being welded, glued, adhered, mechanically crimped, mechanically swaged, braided, physical vapor deposited, chemical vapor deposited, combinations thereof, or the like. In some embodiments, the additional filaments 59b may be formed integrally with the remainder of the device 53, such as being cut from the original sheet or tubing.

In some embodiments, a portion of the protruding section 57 may exhibit a higher porosity than other adjacent portions of the protruding section 57. For example, a first portion of the protruding section 57 may be configured to extend at least partially across a neck of an aneurysm, and have a lower porosity as compared to a second portion of the protruding section 57. With a lower porosity, the first portion may be better capable of scaffolding and supporting embolic material in the aneurysm. With a higher porosity, the second portion of the protruding section 57 may be configured to increase perfusion therethrough.

In some embodiments, at least a portion of the protruding section 57 includes a mesh or cover, such as a polymer covering. In such embodiments, the cover provides a sufficient density that enables the device 53 to act as a scaffolding for embolic material. For example, the cover may have a density greater than about 3% (e.g., about 50%), but it will be appreciated that other densities or porosities are also possible. A higher porosity of at least a portion of the protruding section 57 enables the protruding section 57 to allow perfusion to efferent vessels. For example, a first portion of the protruding section 57 may be configured to extend at least partially across a neck of an aneurysm and may comprise a cover with a density configured to act as a scaffolding for embolic material. A second portion of the protruding section 57, however, may be devoid of a cover, thus enabling the protruding section 57 to increase perfusion therethrough.

In certain embodiments, a percentage of at least a portion of the protruding section 57 covered by the filaments 59a is greater than about 25%, but can also be less than about 40%. In certain embodiments, a percentage of at least a portion of the protruding section 57 covered by the cells 62 is less than about 75%, but can also be greater than about 60%. In certain embodiments, a percentage of at least a portion of the protruding section 57 covered by the filaments 59a is between about 25% and about 40%, and a percentage of at least a portion of the protruding section 57 covered by the cells 62 may be between about 60% and about 75%. Other porosities and densities of the protruding section 57 are also possible, without departing from the scope of the disclosure.

Such filament coverage and/or porosity may advantageously enable at least a portion of the protruding section 57 to divert flow from an aneurysm. Diversion of flow may advantageously allow stagnation of blood flow in the aneurysm, thereby resulting in thrombosis. The illustrated device 53 in FIG. 1A, for example, includes additional filaments 59b covering a portion of the protruding section 57, thereby increasing filament density and enhancing the ability of the protruding section 57 to divert flow from an aneurysm. In some embodiments, at least a portion of the protruding section 57 exhibits a higher porosity than other portions of the protruding section 57 in order to strategically divert flow in certain portions and increase perfusion through other portions.

In some embodiments, the portion of the protruding section 57 that includes a mesh or covering, such as a polymer covering, may also be configured to cause diversion of flow from an aneurysm. For example, the cover may have a porosity that is less than about 25%, and can range to about 0% porosity in some applications. Other porosities are also possible, however, without departing from the scope of the disclosure. In some embodiments, at least a portion of the protruding section 57 is substantially devoid of a mesh or covering or additional filaments 59b. For example, a first portion of the protruding section 57 configured to extend at least partially across a neck of an aneurysm may include a cover that exhibits a porosity configured to divert flow. A second portion of the protruding section 57 may be devoid of the cover in order to increase perfusion therethrough. In certain embodiments, a higher porosity of at least a portion of the protruding section 57 enables the protruding section 57 to allow perfusion to efferent vessels. In yet other embodiments, the mesh or covering over the portion of the protruding section 57 may exhibit a density sufficient to cause diversion of flow into the aneurysm.

Figure 2A:
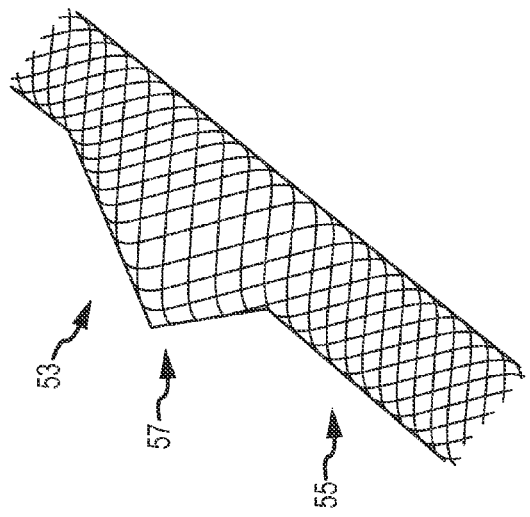
FIG. 2A illustrates an exemplary vascular remodeling device having a protruding section, according to one or more embodiments.
Figure 2B:
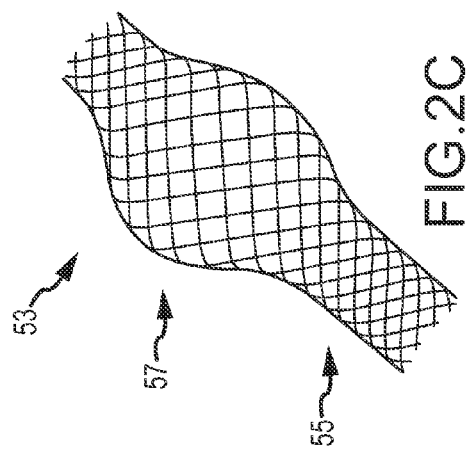
FIG. 2B illustrates another exemplary vascular remodeling device having a protruding section, according to one or more embodiments.
Figure 2C:
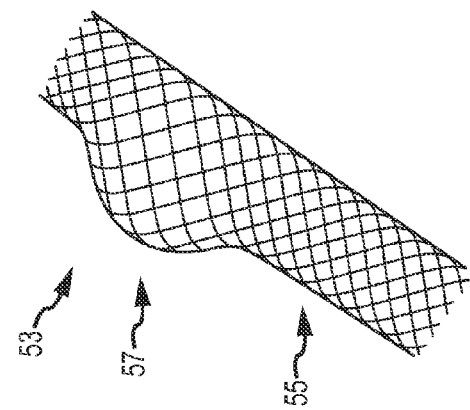
FIG. 2C illustrates another exemplary vascular remodeling device having a protruding section, according to one or more embodiments.

Referring now to FIGS. 2A-2C, illustrated are elevational views of alternative embodiments of the vascular device 53, according to one or more embodiments disclosed. FIG. 2A illustrates the device 53 having a protruding section 57 that bulges radially outward along a portion of the circumference of the device 53 in a generally rounded manner. The device 53 in FIG. 2A may be substantially similar to the device 53 described above with reference to FIG. 1A. For example, the protruding section 57 bulges radially outward along only a portion of its circumference (e.g., along half of the circumference, along a third of the circumference, etc.), but is otherwise substantially co-cylindrical with the first portion 55 along the remaining portion of the circumference. In some embodiments, the protruding section 57 may define a generally symmetric cross-sectional profile, thereby exhibiting a mirror image from a middle point on each axial or longitudinal end of the protruding section 57. In such an embodiment, the protruding section 57 may be configured to bulge radially outward so that the outward-most point or area is located substantially at the center of the protruding section 57.

In FIG. 2B, the protruding section 57 may be configured to bulge radially outward towards a point or a line. As illustrated, the resulting bulge of the protruding section may provide the general shape of a pyramid or prism, for example, Again, the protruding section 57 may radially bulge about only a portion of the radial circumference of the device 53 or about the entirety thereof, without departing from the scope of the disclosure. In some embodiments, the protruding section 57 may be configured to bulge radially outward in a non-uniform manner, such as randomly, towards a series of points, towards a curve, combinations thereof, etc. Other embodiments of protruding sections 57 with generally symmetric profiles are also possible (e.g., toroidal bulging).

In at least one embodiment, the protruding section 57 shown in FIG. 2B has a generally asymmetric cross-sectional profile, where opposing sections extending from a middle point of the protruding section 57, either axially or longitudinally, are substantially dissimilar. For example, the protruding section 57 may bulge outwardly so that the outward most point or area is located away from a point or line or area at the true center of the protruding section 57. As another example, the protruding section 57 may bulge outwardly in a non-uniform manner. As yet another example, the protruding section 57 may be defined by two or more bulges or protrusions, where the multiple protrusions are not equidistantly or equally spaced about the middle or center of the protruding section 57.

Referring to FIG. 2C, the device 53 may be configured such that the protruding section 57 bulges out radially about the entire circumference of the device 53. Such embodiments may allow for convenient positioning at the aneurysm since axial rotational orientation of the device 53 may not be required. For example, upon deployment at a bifurcation, the protruding section 57 may be configured to flatten along one longitudinal side due to contact with the vasculature while the opposing longitudinal side may extend at least partially into the aneurysm or bifurcation as desired. Flexibility and compliance of the device 53 may reduce or otherwise minimize damage to the surrounding vasculature.

It will be appreciated that combinations of the various protruding sections 57 described herein are possible, without departing from the scope of the disclosure. For example, the protruding section 57 may be asymmetrical, symmetrical, bulge towards a line or ring around the entire circumference of the device 53, and/or have a first portion that bulges towards a line and a second portion that bulges in a generally rounded or arcuate manner.

Figure 3B:
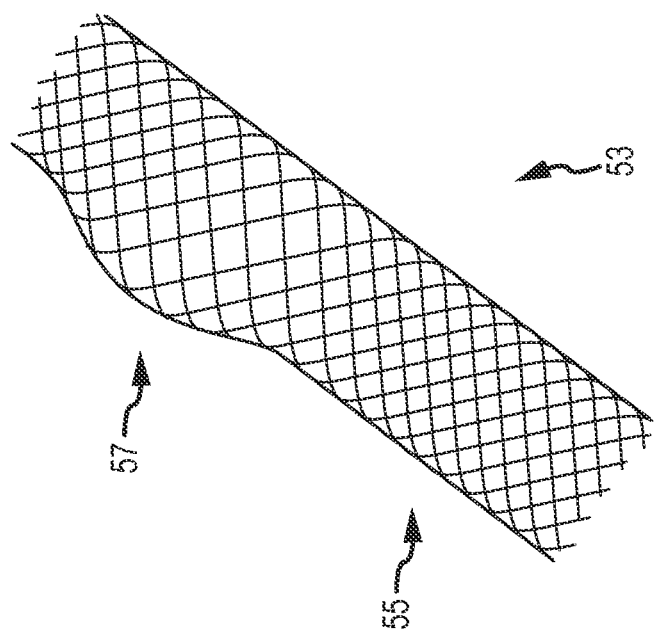
FIG. 3B illustrates the vascular remodeling device of FIG. 3A having the protruding section in its further expanded configuration, according to one or more embodiments.
Figure 3A:
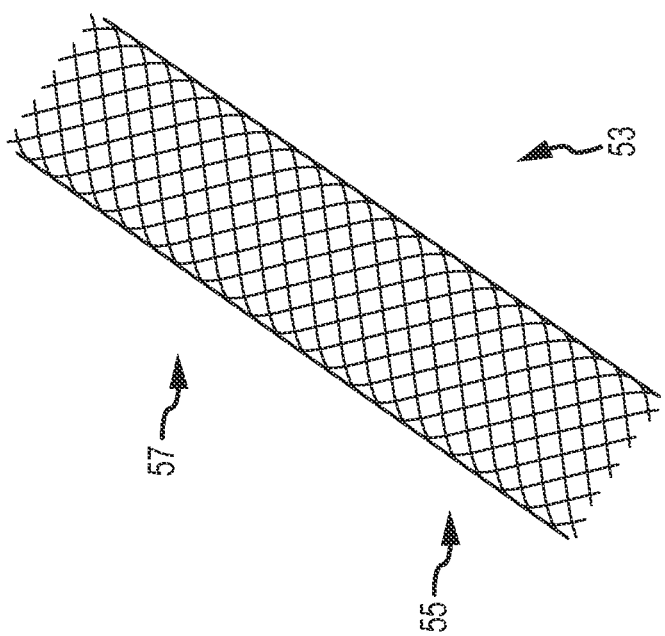
FIG. 3A illustrates an exemplary vascular remodeling device in its expanded configuration, according to one or more embodiments.

Referring now to FIGS. 3A and 3B, illustrated is an example of how the protruding section 57 of the device 53 may achieve a further expanded configuration, according to one or more embodiments. FIG. 3A illustrates the device 53 upon deployment from a catheter or other delivery tubular or device, in which the first section 55 has expanded from its compressed configuration to its expanded configuration. At this point, the protruding section 57 may be considered to have expanded from a compressed configuration to an intermediate or semi-expanded configuration, but has not yet assumed a further expanded configuration.

FIG. 3B depicts the protruding section 57 in its further expanded configuration in which the protruding section 57 bulges or otherwise protrudes radially outward from the first section 55. It will be appreciated that the protruding section 57 may be configured to expand from its compressed configuration directly to its further expanded configuration, without requiring the device 53 to transition between its compressed and expanded configurations. The device 53 may be configured to be self-expanding under certain conditions, such as when not restrained by a catheter, or when coming into contact with an external stimulus such as heat or a chemical agent. In at least one embodiment, the device 53 may be configured to expand when coming into contact with a warm fluid, such as saline. In embodiments where the device 53 is deployed from a catheter, the protruding section 57 may be adapted to expand into its further expanded configuration after being released from the catheter, while a portion of the first section 55 is still compressed within the catheter. With the portion of the first section 55 remaining in the catheter, the device may be able to be resheathed or otherwise retracted back into the catheter for repositioning.

In some embodiments, the density of the filaments 59b (FIG. 1A) in the protruding section 57 may be configured such that when the device 53 is in its compressed configuration, or otherwise prior to expanding into its further expanded configuration, the filaments 59b may exhibit a lower porosity or small pore or cell size. In other words, in the compressed configuration or antecedent to its further expanded configuration, the protruding section 57 may exhibit less porosity than the first section 55 (FIG. 1A). However, upon full expansion to the further expanded configuration, the density of the filaments 59b in the protruding section 57 may be configured such that the porosity or cell sizes of the device 53 along its entire axial length is equal or substantially equal. Accordingly, in at least one embodiment, the porosity of the filaments 59a of the first section 55 and the porosity of the filaments 59b of the protruding section 57 may be approximately the same when the device 53 expands to the further expanded configuration. An example of such an embodiment may be generally shown in the cell pattern 66l described below with reference to FIG. 6L.

In some embodiments, in a compressed configuration, the first section 55 has a first compressed porosity, a first compressed cell size, and a first compressed cross-sectional dimension. In the compressed configuration the protruding section 57 has a second compressed porosity, a second compressed cell size, and a second compressed cross-sectional dimension.

The first compressed porosity may be greater than the second compressed porosity. The first compressed cell size may be greater than the second compressed cell size. The first compressed cross-sectional dimension may be substantially equal to the second compressed cross-sectional dimension.

In some embodiments, in an expanded configuration, the first section 55 has a first expanded porosity, a first expanded cell size, and a first expanded cross-sectional dimension. In the expanded configuration, the protruding section 57 has a second expanded porosity, a second expanded cell size, and a second expanded cross-sectional dimension.

The first expanded porosity may be substantially equal to the second expanded porosity. The first expanded cell size may be substantially equal to the second expanded cell size. The first expanded cross-sectional dimension may be less than the second expanded cross-sectional dimension.

In some embodiments, the device 53 may be made of a self-expanding, super elastic, and/or a shape-memory material such as, but not limited to, nitinol, CoCr alloys, shape memory polymers (e.g., polyglycolic acid, polylactic acid), combinations thereof, or the like. In at least one embodiment, the first section 55 and the protruding section 57 may be made of different materials. For example, the first section 55 may be made of a polymer material while the protruding section 57 may be made of a metallic material or a different polymer material. Other combinations of materials are also possible, without departing from the scope of the disclosure.

In some embodiments, the device 53 may be at least partially made from, or at least carry with it, a radiopaque marker or material such as platinum, platinum-iridium, and/or tantalum. In one embodiment, the filaments 59a may be radiopaque markers. In other embodiments, certain segments or portions of the protruding section 57 may be made of or include radiopaque markers in the form of marker coils and/or marker bands. In yet other embodiments, the filaments 59a and certain segments of the protruding section 57 may be made of or otherwise include radiopaque markers. In yet other embodiments, the filaments 59a or other structural components of the protruding section 57 may be made of a radiopaque material.

Referring now to FIGS. 4A and 4B, illustrated is an exemplary method or process for treating an aneurysm 10 using the vascular device 53 as generally described herein, according to one or more embodiments. As illustrated, the device 53 may be positioned within a patient's vasculature at a bifurcation 71, such as at a neurovascular bifurcation (e.g., the basilar tip area). The bifurcation 71 may include an afferent vessel 67, two or more efferent vessels 68a, 68b, and an aneurysm 10. The first section 55 may be configured or otherwise dimensioned to fit within the afferent vessel 67. For example, the diameter of the afferent vessel 67 may range between about 2 mm and about 12 mm, between about 6 mm and about 8 mm, less than about 15 mm, or greater than about 1 mm, and the first section 55 may be suitably dimensioned to expand and fit the afferent vessel 67.

In some embodiments, a portion of the protruding section 57 may extend at least partially across an ostium of one of the efferent vessels, such as the second efferent vessel 68b. In such embodiments, at least a portion of the protruding section 57 may have a lower density than other portions of the protruding section 57 to allow perfusion to the second efferent vessel 68b. The device 53 may be configured to reduce the effective width of the neck of the aneurysm 10. For example, the device 53 may be configured to act as a scaffolding that inhibits or otherwise prevents herniation or prolapse of objects 69 (FIG. 4B), such as embolization coils or thrombi, out of the aneurysm 10.

At least a portion of the protruding section 57 may be dense enough that such objects 69 cannot pass therethrough. In some embodiments, however, the protruding section 57 may be configured to allow the insertion of embolic material therethrough and into the aneurysm 10. For example, embolic material 69 may be inserted or otherwise delivered into the aneurysm 10 through the cells 62 (FIG. 1A) defined between adjacent filaments 59a, 59b (FIG. 1A) or other structural components of the protruding section 57.

In some embodiments, a relative amount of the protruding section 57 or a portion thereof occupied by the filaments 59a, 59b (FIG. 1A), or other structural components of the protruding section 57, is between about 3% and about 25%. In some embodiments, a relative amount of the protruding section 57 or a portion thereof occupied by the filaments 59a, 59b, or other structural components of the protruding section 57, is between about 3% and about 15%. In some embodiments, a relative amount of the protruding section 57 or a portion thereof occupied by the filaments 59a, 59b, or other structural component of the protruding section 57, is at least about 5%.

FIG. 4A depicts the first section 55 as it is anchored in the afferent vessel 67 and the protruding section 57 as it is arranged at the junction of the bifurcation 71 and across the neck of the aneurysm 10. As illustrated, the first section 55 is in its expanded configuration and the protruding section 57 is in its further expanded configuration. To anchor the first section 55 in the afferent vessel 67, the distal tip of a delivery catheter (not shown), such as microcatheter, is tracked through the vasculature to reach the location of the bifurcation 71. The device 53 is deployed out of the distal end of the catheter 60, thereby allowing the device 53 to expand. The protruding section 57 expands and further expands at or near the junction of the bifurcation 71 and either at least partially inside the aneurysm 10 or across the neck of the aneurysm 10. The first section 55 expands within the afferent vessel 67 and thereby anchors the device 53. The protruding section 57 acts as scaffolding to inhibit herniation or prolapse of objects 69 (e.g., embolic material, thrombi, etc.) from the aneurysm 10 and simultaneously allows perfusion to the efferent vessels 68*a,b*.

In one or more embodiments, the device 53 is able to be fully retrieved inside the catheter whereupon the position of the catheter can be adjusted and the device 53 can be redeployed at a more desirable position within the vasculature. In other embodiments, the device 53 may be retracted into the catheter so as to be repositioned in a new axial rotational position, for example, more proximal or distal to the afferent vessel 67 and/or the efferent vessel(s) 68*a,b*, etc. Additionally or alternatively, the device 53 can be fully retrieved inside the catheter and a different catheter or the same catheter with a different device having different dimensions (e.g., diameter, length, etc.) or exhibiting different more desirable properties (e.g., better anchoring, better neck coverage, etc.) can be deployed at a more desirable position within the vasculature. Once the device 53 is accurately positioned, the device 53 can be detached from the catheter electrolytically (e.g., by applying a small current until a proximal tip of the device 53 corrodes away), mechanically (e.g., by a release mechanism), or chemically (e.g., by dissolving a connecting portion with a biocompatible solvent such as DMSO), thereby permanently placing the device 53 at the junction of the bifurcation 71. As will be appreciated, other detachment mechanisms are also possible.

The protruding section 57 includes transition portions on both sides of the section 57 that transition to the shape of the remaining shape of the device 53. In some embodiments, the transition portions can include a taper from an outer extent of the protruding section 57 down to the surface of the remaining shape of the device 53 (e.g., the first section 55). In some embodiments, a taper on a distal portion of the protruding section 57 can be the same as a taper on a proximal portion of the protruding section 57. In some embodiments, the distal portion can taper at a steeper degree than the proximal portion taper. The difference in taper can skew the protruding portion toward the side having a steeper degree of taper. In some embodiments, the steeper taper can be used to extend across the aneurysm ostium as the device 53 curves along the bifurcation.

FIG. 4B illustrates a plurality of embolization coils 69 inserted in the fundus of the aneurysm 10. The embolization coils 69 may be a single embolization coil or other embolic material. The embolization coils 69 or other embolic material may be inserted into the fundus before, during, and/or after the device 53 is positioned within the vasculature. In some embodiments, the embolization coils 69 are inserted in the fundus of the aneurysm 10 using the same catheter from which the device 53 is deployed.

As described herein, the protruding section 57 may perform a variety of functions, for example, providing support to the embolic material 69, allowing perfusion to the efferent vessels 68*a,b*, reducing the effective width of the neck of the aneurysm 10, and/or inhibiting the prolapse of objects 69 from the neck of the aneurysm 10. The protruding section 57 may be atraumatic and made of flexible materials or otherwise forming atraumatic shapes in order to inhibit damaging or rupturing the aneurysm 10. In one or more embodiments, the protruding section 57, or portions thereof, may be self-conforming to irregular contours of aneurysm 10, the neck of the aneurysm 10, or the bifurcation 71.

As illustrated, the protruding section 57 may bulge radially outward from the first section 55 and extend partially within the aneurysm 10 in a generally rounded manner. In use, the protruding section 57 may serve as a scaffolding section that maintains the embolization coils 69 within the fundus of the aneurysm 10 or otherwise allows for the safe and controlled placement of such embolization coils 69 therein. The protruding section 57 may also be configured to allow perfusion to the efferent vessels 68*a,b*.

Figure 5:
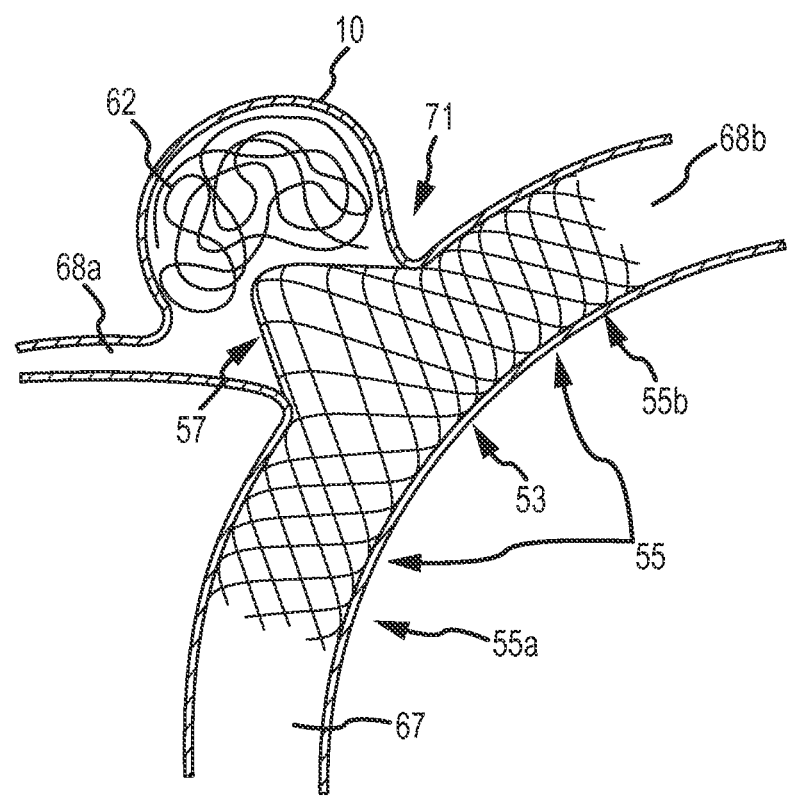
FIG. 5 illustrates an exemplary vascular remodeling device as deployed at a bifurcation having an aneurysm, according to one or more embodiments disclosed.

Referring now to FIG. 5, illustrated is another application of the exemplary vascular device 53, according to one or more embodiments. As illustrated, the device 53 is positioned at a bifurcation 71 having an afferent vessel 67, two or more efferent vessels 68*a*, 68*b*, and an aneurysm 10. The first section 55 of the device 53 may include a proximal portion 55*a* and a distal portion 55*b* that anchor the device 53 on either or both sides of the bifurcation 71. Accordingly, the first section 55 extends longitudinally from both axial ends or sides of the protruding section 57, which may help to properly position the protruding section 57. The first section 55 may be flexible and yet have enough radial force to anchor or maintain the position of the device 53 at the bifurcation 71 after deployment, thereby inhibiting or preventing longitudinal migration of the device 53.

Anchoring the distal portion 55*b* in the efferent vessel 68*b* may be accomplished as follows. The distal tip of a delivery catheter (not shown), such as a microcatheter or other delivery device that can be tracked through the vasculature, is positioned within the efferent vessel 68*b* adjacent the aneurysm 10. The device 53 is then deployed out of the distal end of the catheter, thereby allowing the device 53 to expand either automatically or as a result of coming into contact with an external stimulus (e.g., temperature or chemical stimuli). The distal portion 55*b* expands within the efferent vessel 68*b* and may serve to anchor the device 53 therein. As the protruding section 57 exits the catheter, it may expand to its intermediate expanded configuration and thereafter expand even more to the further expanded configuration.

In its further expanded configuration, the protruding section 57 may extend within the junction of the bifurcation 71 and at least partially across the neck of the aneurysm 10. The proximal portion 55*a* thereafter exits the catheter and correspondingly expands within the afferent vessel 67 and may serve to anchor the device 53 therein also. Accordingly, the distal portion 55*b* is anchored in the efferent vessel 68*b*, the proximal portion 55*a* is anchored in the afferent vessel 67, and the protruding section 57 acts as scaffolding to inhibit herniation or prolapse of embolic material 69 from the aneurysm 10 and allows perfusion to the efferent vessels 68*a*, 68*b*.

As in prior embodiments, the device 53 can be fully retrieved or otherwise resheathed inside the catheter and the device 53 can be redeployed, for example, at a more desirable or accurate position. Moreover, as also in prior embodiments, final release of the device 53 from the catheter may be mechanical, electrolytic, and/or chemical.

Referring now to FIGS. 6A-6L, illustrated are exemplary patterns of cells defined by the cutting, depositing, meshing and/or weaving one or more filaments 59*a*, 59*b* on the first and/or second sections 55, 57, according to one or more embodiments. Specifically, various exemplary cell patterns 66*a*, 66*b*, 66*c*, 66*d*, 66*e*, 66*f*, 66*g*, 66*h*, 66*i*, 66*j*, 66*k*, 66*l* are illustrated that may be incorporated into the vascular device 53 as generally described herein to achieve the desired functionality described above. Alternatively, these cell patterns 66*a-l* may be used in other types of stents and/or vascular devices such as, but not limited to, stents having a generally a generally uniform outside diameter along their length.

FIG. 6A illustrates an exemplary cell pattern 66*a* that has an "open cell" design. As illustrated, the cell pattern 66*a* may be identifiable by the reverse free-peaks 74 and the forward free-peaks 99. In operation, open cell designs generally provide good flexibility and wall apposition, but may be difficult to retrieve, for example due to the potential of the reverse free-peaks 74 of snagging or catching on the catheter during retrieval.

FIG. 6B illustrates an exemplary cell pattern 66*b* that has a "closed cell" design. As illustrated, the cell pattern 66*b* may be identifiable by the lack of any peaks due to contact of all defined cells at corresponding intersections 101. FIG. 6C illustrates another exemplary cell pattern 66*c* that has a "closed cell" design. The cell pattern 66*c* may be identifiable by the lack of reverse free-peaks 103 and forward free-peaks 108, which are instead connected by one or more filaments 105. As will be appreciated, closed cell designs are generally easy to deliver and to retrieve, but may be stiff and provide poor wall apposition. As a result, some closed cell designs may be prone to kinking rather than bending.

FIGS. 6D-6H illustrate exemplary cell pattern embodiments that are "hybrid" or "combination" designs that include features of open and closed cell designs. As will be appreciated, a hybrid of open cell and closed cell designs can advantageously incorporate the advantages of each design and simultaneously avoid the potential drawbacks of each design. FIG. 6D illustrates an exemplary cell pattern 66*d* that has a hybrid cell design. For example, the cell pattern 66*d* may include forward connected peaks 131, 133, forward free-peaks 132, and reverse connected peaks 134. As illustrated, the forward peaks 133 may be connected to the next unit cell. The cell pattern 66*d*, however, does not include any reverse free-peaks, such as the reverse free peaks 74 of FIG. 6A.

FIG. 6E illustrates an exemplary cell pattern 66*e* that also has a hybrid cell design. Similar to the cell pattern 66*d* described above with reference to FIG. 6D, the cell pattern 66*e* may include forward connected peaks 131, 133, forward free-peaks 132, and reverse connected peaks 134. As illustrated, the forward peaks 133 may be connected to the next unit cell, but the cell pattern 66*e* does not include any reverse free-peaks, such as the reverse free peaks 74 of FIG. 6A.

FIG. 6F illustrates an exemplary cell pattern 66*f* that also has a hybrid cell design. As illustrated, the cell pattern 66*f* may include forward connected peaks 131, forward free-peaks 132, and reverse connected peaks 134. The cell pattern 66*f* may further include valleys 135 connected to the next unit cell. The cell pattern 66*f*, however, does not include any reverse free-peaks, such as the reverse free peaks 74 of FIG. 6A.

FIG. 6G illustrates an exemplary cell pattern 66*g* that also has hybrid cell design. Similar to the cell pattern 66*f* described above with reference to FIG. 6F, the pattern 66*g* may include forward connected peaks 131, forward free-peaks 132, and reverse connected peaks 134. As illustrated, the cell pattern 66*g* may also include valleys 135 connected to the next unit cell, but the cell pattern 66*g* does not include any reverse free-peaks, such as the reverse free peaks 74 of FIG. 6A.

FIG. 6H illustrates an exemplary cell pattern 66*h* that also has a hybrid cell design. As illustrated, the cell pattern 66*h* may include forward connected peaks 133, forward free-peaks 132, and reverse connected peaks 134. The forward peaks 133 may be connected to the next unit cell, and each unit cell may include forward connected peaks 133 alternating with forward free-peaks 132. Moreover, the cell pattern 66*h* may further include peaks connected to the next unit cell. The cell pattern 66*h*, however, does not include any reverse free-peaks, such as the reverse free peaks 74 of FIG. 6A.

FIG. 6I illustrates an exemplary cell pattern 66*i* that also has a hybrid cell design. As illustrated, the cell pattern 66*i* may include forward connected peaks 133, forward free-peaks 132, and reverse connected peaks 134. The forward peaks 133 may be connected to the next unit cell, and each unit cell may include forward connected peaks 133 alternating with forward free-peaks 132. The cell pattern 66*i* may further include peaks connected to the next unit cell, but the cell pattern 66*i* does not include any reverse free-peaks, such as the reverse free peaks 74 of FIG. 6A. In contrast to the cell pattern 66*h* of FIG. 6H, the cell pattern 66*i* of FIG. 6I has fewer diagonal filaments (e.g., missing in the indicated area 138), which may provide increased flexibility and/or wall apposition.

FIG. 6J illustrates an exemplary cell pattern 66*j* that also has a hybrid cell design. As illustrated, the cell pattern 66*j* may include forward connected peaks 133, forward free-peaks 132, and reverse connected peaks 134. The forward connected peaks 133 may be connected to the next unit cell, and each unit cell may include forward connected peaks 133 alternating with forward free-peaks 132. The cell pattern 66*j* may further include peaks connected to the next unit cell, however, the cell pattern 66*j* does not include any reverse free-peaks, such as the reverse free peaks 74 of FIG. 6A. In contrast to the cell pattern 66*i* of FIG. 6I, the cell pattern 66*j* of FIG. 6J may not include one or more straight filaments 109, which may help the cell pattern 66*i* be less prone to twisting during compaction.

FIG. 6K illustrates an exemplary cell pattern 66*k* that also has a hybrid or combination cell design. As illustrated, the cell pattern 66*k* may include a plurality of reverse free peaks 74, a plurality of reverse connected peaks 134, and a plurality of forward connected peaks 133. Across at least a circumferential portion of the cell pattern 66*k*, the reverse free peaks 74 may alternate with the reverse connected peaks 134. In some cases, the forward and reverse connected peaks 131, 134 are coupled with a straight filament 109 configured to enlarge the size of the cells and help the cell pattern 66*k* be less prone to twisting during compaction. The cell pattern 66*k*, however, may not include forward free peaks 132, as in cell pattern 66*d* described above with reference to FIG. 6D.

Referring briefly to FIG. 7A, with continued reference to FIG. 6K, illustrated is an exemplary vascular remodeling device 53 that employs the cell pattern 66*k*, and is shown as being in its further expanded configuration. As illustrated, the device 53 includes a plurality of reverse free and connected peaks 74, 134 and a plurality of forward connected peaks 133, where the reverse free peaks 74 are configured to alternate with the reverse connected peaks 134. Moreover, a plurality of straight filaments 109 serve to connect many of the forward and reverse connected peaks 131, 134 in several areas about the circumference of the device 53.

FIG. 6L illustrates an exemplary cell pattern 66*l* that also has a hybrid or combination cell design. As illustrated, the cell pattern 66*l* may include a plurality of reverse free peaks 74, a plurality of reverse connected peaks 134, a plurality of forward free peaks 132, and a plurality of forward connected peaks 133. The reverse and forward connected peaks 134, 133 may be coupled together at their various locations about the circumference of the cell pattern 66*l*. Unlike cell pattern 66*k*, however, the cell pattern 66*l* does not necessarily include one or more straight filaments 109.

Referring briefly to FIG. 7B, with continued reference FIG. 6L, illustrated is an exemplary vascular remodeling device 53 that employs the cell pattern 66*l*, and is shown as being in its further expanded configuration. As illustrated, the device 53 may be substantially similar to the device 53 shown above in FIG. 2C, where the protruding section 57 bulges out radially about the entire circumference of the device 53. Specifically, the device 53 shown in FIG. 7B may include a plurality of reverse free and connected peaks 74, 134 and a plurality of forward free and connected peaks 132, 133. The reverse and forward connected peaks 134, 133 may be coupled together at various locations about the circumference of the device 53, as indicated.

Combinations of the features of the various cell patterns illustrated in FIGS. 6A-6L may be selected based on desired structural properties of the first section 55 and the protruding section 57 (FIG. 1A). For example, the first section 55 may include an open cell design and the protruding section 57 may include a closed cell design, or vice versa. In other embodiments, the first section 55 may include an open or a closed cell design and the protruding section 57 may include a hybrid cell design, or vice versa. In other embodiments, both the first and protruding sections 55, 57, may include an open or a closed cell design. In yet other embodiments, both the first and protruding sections 55, 57 may include a hybrid cell design.

Embodiments of the device 53 in which the first section 55 extends longitudinally from the protruding section 57 on one side and is configured to anchor in an afferent vessel may comprise a hybrid cell design in at least a portion of the first section 55. A hybrid cell design may advantageously provide good flexibility and/or good wall apposition of the first section 55 in the afferent vessel and/or have good retrieval characteristics due to the lack of reverse free-peaks. For example, the protruding section 57 may expand in the junction (e.g., a bifurcation having an aneurysm) and the first section 55 may expand in the afferent vessel, after which at least a portion of the first section 55 may be at least partially retrieved back into the catheter.

In some embodiments, the device 53 may include a hybrid cell design in the first section 55 and a hybrid cell design in the protruding section 57. A hybrid cell design in the protruding section 57 may advantageously provide good retrieval characteristics. For example, the protruding section 57 may expand in the junction (e.g., a bifurcation having an aneurysm) and the first section 55 may expand in the afferent vessel, after which the first section 55 and at least a portion of the protruding section 57 may be at least partially retrieved back into the catheter.

In some embodiments, the device 53 may include a hybrid cell design in the first section 55 and a closed cell design in the protruding section 57. A closed cell design in the protruding section 57 may advantageously provide good retrieval characteristics and may lack disadvantages that may be associated with closed cell designs. For example, the protruding section 57 may expand in the junction (e.g., a bifurcation having an aneurysm), where flexibility and wall apposition may be less important and/or where rigidity may be advantageous, and the first section 55 may expand in the afferent vessel, after which the first section and at least a portion of the protruding section may be at least partially retrieved back into the catheter.

In some embodiments, the device 53 may include a hybrid cell design in the first section 55 and an open cell design in the protruding section 57. An open cell design in the protruding section 57 may advantageously provide good flexibility. For example, the protruding section 57 may expand in the junction (e.g., a bifurcation having an aneurysm) and/or at least partially within an aneurysm, during which the flexible protruding section 57 may better conform to the shape of the junction and/or reduce the likelihood of puncturing the aneurysm. Moreover, the first section 55 may expand in the afferent vessel after which at least a portion of the first section 55 may be at least partially retrieved back into the catheter.

As will be appreciated, combinations of cell designs within each of the first section 55 and the protruding section 57 are also possible, without departing from the scope of the disclosure. For example, a proximal portion of the first section 55 may have a hybrid cell design and a distal portion of the first section 55 may have an open cell design. In other embodiments, a first portion of the protruding section 57 may be configured to allow perfusion to branch vessels and may have a hybrid cell design, and a second portion of the protruding section 57 may be configured to act as a scaffolding and may have a closed cell design.

Embodiments of the device 53 in which the first section 55 extends longitudinally past the protruding section 57 on one side and is configured to anchor in an efferent vessel may include a hybrid cell design in at least a portion of the protruding section 57 to advantageously exhibit good retrieval characteristics (e.g., due to the lack of reverse free-peaks). For example, the first section 55 may expand in the efferent vessel and the protruding section 57 may expand in the junction (e.g., a bifurcation having an aneurysm), after which at least a portion of the protruding section 57 may be at least partially retrieved back into the catheter.

In some embodiments, the device 53 may include a hybrid cell design in the protruding section 57 and a hybrid cell design in the first section 55. A hybrid cell design in the first section 55 may advantageously provide good flexibility and/or wall apposition of the first section 55 in the efferent vessel and/or good retrieval characteristics. For example, the first section 55 may expand in the efferent vessel and the protruding section 57 may expand in the junction (e.g., a bifurcation having an aneurysm), after which the protruding section 57 and at least a portion of the first section 55 may be at least partially retrieved back into the catheter.

In some embodiments, the device 53 may include a hybrid cell design in the first section 55 and a closed cell design in the protruding section 57. A closed cell design in the first section 55 may advantageously provide good retrieval characteristics. For example, the first section 55 may expand in the efferent vessel and the protruding section 57 may expand in the junction (e.g., a bifurcation having an aneurysm), after which the protruding section 57 and at least a portion of the first section 55 may be at least partially retrieved back into the catheter.

In some embodiments, the device 53 may include a hybrid cell design in the protruding section 57 and an open cell design in the first section 55. An open cell design in the first section 55 may advantageously provide good flexibility and/or wall apposition. For example, the first section 55 may anchor in the efferent vessel and the protruding section 57 may expand in the junction (e.g., a bifurcation having an aneurysm), after which the portion of the protruding section 57 may be at least partially retrieved back into the catheter.

As will be appreciated, various combinations of cell designs within each of the protruding section 57 and the first section 55 are also possible, without departing from the scope of the disclosure. For example, a proximal portion of the protruding section 57 may have a hybrid cell design and a distal portion of the protruding section 57 may have an open cell design. As another example, a first portion of the protruding section 57 configured to allow perfusion to branch vessels may have a hybrid cell design and a second portion of the protruding section 57 configured to act as a scaffolding may have a closed cell design.

In embodiments of the device 53 in which the first section 55 extends longitudinally from both sides of the protruding section 57 (e.g., the proximal portion 55a and the distal portion 55b shown in FIG. 5), and is configured to anchor in at least one of an afferent vessel and an efferent vessel, at least a portion of the proximal portion 55a may include a hybrid cell design. The hybrid cell design may advantageously provide good flexibility and/or wall apposition of the first section 55 in the afferent vessel and/or have good retrieval characteristics (e.g., due to the lack of reverse free-peaks). For example, the distal portion 55b may expand in the efferent vessel, the protruding section 57 may expand in the junction, and the proximal first section may expand in the afferent vessel, after which at least a portion of the proximal portion 55a may be at least partially retrieved back into the catheter.

In some embodiments, the device 53 may include a hybrid cell design in the proximal portion 55a and a hybrid cell design in the protruding section 57. The hybrid cell design in the protruding section 57 may advantageously provide good retrieval characteristics. For example, the distal portion 55b may expand in the efferent vessel, the protruding section 57 may expand in the junction, and the proximal portion 55a may expand in the afferent vessel, after which the proximal portion 55a and at least a portion of the protruding section 57 may be at least partially retrieved back into the catheter.

In some embodiments, the device 53 may include a hybrid cell design in the first section 55 (e.g., the proximal and distal portions 52a,b) and in the protruding section 57. For example, in embodiments of the device 53 in which the first section 55 anchors in the afferent and efferent vessels, the hybrid cell design in the distal portion 55b may advantageously provide good flexibility and/or good wall apposition in the distal portion 55b and/or have good retrieval characteristics (e.g., due to the lack of reverse free-peaks). Moreover, the distal portion 55b may anchor in the efferent vessel, the protruding section 57 may expand in the junction, and the proximal portion 55a may anchor in the afferent vessel, after which the proximal portion 55a, the protruding section 57, and at least a portion of the distal portion 55b may be at least partially retrieved back into the catheter.

In some embodiments, the device 53 may include a hybrid cell design in at least a portion of the proximal portion 55a and a closed cell design in the protruding section 57. A closed cell design in the protruding section 57 may advantageously provide good retrieval characteristics and may lack the disadvantages that may be associated with closed cell designs. The distal portion 55b may expand in the efferent vessel, the protruding section 57 may expand in the junction where flexibility and wall apposition may be less important and/or where rigidity may be advantageous, and the proximal portion 55a may expand in the afferent vessel. During delivery, the proximal portion 55a and at least a portion of the protruding section 57 may be at least partially retrieved back into the catheter for repositioning. In other embodiments, the proximal portion 55a, the protruding section 57, and at least a portion of the distal portion 55b may be at least partially retrieved back into the catheter.

In some embodiments, the device 53 may include a hybrid cell design in the proximal portion 55a and a closed cell design in at least a portion of the distal portion 55b. The closed cell design in the distal portion 55b may advantageously provide good retrieval characteristics. In embodiments in which the distal portion 55b does not anchor in an efferent vessel, a closed cell design in the distal portion 55b may advantageously lack disadvantages that may be associated with closed cell designs. For example, the distal portion 55b may expand in the efferent vessel without contacting or conforming to the walls of the efferent vessels but still providing a fluid flow path from the afferent vessel to the efferent vessel, the protruding section 57 may expand in the junction, and the proximal portion 55a may anchor in the afferent vessel. After full or partial expansion of the device 53, the proximal portion 55a, the protruding section 57, and at least a portion of the distal portion 55b may be at least partially retrieved back into the catheter for repositioning.

In some embodiments, the device 53 may include a hybrid cell design in at least a portion of the distal portion 55b and a closed cell design in at least a portion of the proximal portion 55a. The closed cell design in the proximal portion 55a may advantageously provide good retrieval characteristics. In embodiments in which the proximal portion 55a does not anchor in the afferent vessel, a closed cell design in the proximal portion 55a may advantageously lack disadvantages that may be associated with closed cell designs. A hybrid cell design in the distal portion 55b may advantageously provide good flexibility and/or good wall apposition in the distal portion 55b and/or have good retrieval characteristics. For example, the proximal portion 55a may expand in the afferent vessel without contacting or conforming to the walls of the afferent vessel but still providing a fluid flow path from the afferent vessel to the efferent vessels, the protruding section 57 may expand in the junction, and the distal portion 55b may anchor in the efferent vessel. After expansion of the device 53, the proximal portion 55a, the protruding section 57, and at least a portion of the distal portion 55b may be at least partially retrieved back into the catheter.

In some embodiments, the device 53 may include a hybrid cell design in at least a portion of the proximal portion 55a and an open cell design in the protruding section 57. An open cell design in the protruding section 57 may advantageously provide good flexibility. For example, the distal portion 55b may expand in the efferent vessel, the protruding section 57 may expand in the junction and/or at least partially within an aneurysm, during which the flexible protruding section 57 may better conform to the shape of the junction and/or reduce the likelihood of puncturing the aneurysm, and the proximal portion 55a may expand in the afferent vessel. After partial or full deployment of the device 53, at least a portion of the proximal portion 55a may be at least partially retrieved back into the catheter.

In some embodiments, the proximal portion 55a comprises a hybrid cell design and at least a portion of the distal portion 55b comprises an open cell design. An open cell design in the distal portion 55b may advantageously provide good flexibility and/or wall apposition. These advantages may be beneficial in embodiments in which the distal portion 55b anchors in an efferent vessel. For example, the proximal portion 55a may anchor in the afferent vessel, the protruding section 57 may expand in the junction, and the distal portion 55b may anchor in the efferent vessel, after which the proximal portion 55a, the protruding section 57, and at least a portion of the distal portion 55b may be at least partially retrieved back into the catheter.

It will be appreciated that combinations of cell designs within each of the protruding section 54, the proximal portion 55a, and the distal portion 55b are also possible, without departing from the scope of the disclosure. For example, a more proximal section of the proximal portion 55a may have a hybrid cell design and a distal section of the proximal portion 55a may have an open cell design. As another example, a first portion of the protruding section 57 configured to allow perfusion to branch vessels may have a hybrid cell design and a second portion of the protruding section 57 configured to act as a scaffolding may have a closed cell design.

Referring again to FIGS. 6B, 6D, 6F, and 6K, the illustrated cell patterns 66b, 66d, 66f, 66k, respectively, each have one tapered section 71. The illustrated cell patterns 66a, 66c, 66e,

66g, 66h, 66i, 66j in FIGS. 6A, 6C, 6E, 6G, 6H, 6I, and 6J, respectively, however, have two tapered sections 71. The tapered sections 71 may allow the device 53 or portions thereof (e.g., the first section 55, the protruding section 57, etc.) to be retrieved back into a catheter for repositioning. For example, if the device 53 is being pulled into a catheter, the tapered portions 71 may radially compress the first section 55, thereby facilitating easier retrieval back into the catheter.

A single tapered section 71 may advantageously have only one detachment zone or location and be easy to release, while a plurality of tapered sections 71 may include a detachment zone or location proximal to each tapered section 71 and may be more difficult to release. In one or more embodiments, the plurality of tapered sections 71 may exhibit a shorter taper length but simultaneously provide a longer effective length. Moreover, the single tapered section 71 may exhibit a longer taper length but and a shorter effective length, thereby facilitating less anchoring effect in the vasculature.

In some embodiments, the plurality of tapered sections 71 may be more symmetrical and provide more uniform wall apposition than embodiments of the device 53 having only a single tapered section 71. Moreover, the plurality of tapered sections 71 may exhibit less tension on the vasculature, which may result from a single long tapered area applying force to a single side of the vasculature. The effective length of the device 53 may be based on the intended anatomy. For example, longer lengths may be appropriate for more vessel wall apposition, while shorter lengths may be appropriate for traversing more tortuous anatomy.

Referring again to FIGS. 6C, 6F, and 6G, the illustrated cell patterns 66c, 66f, 66g, respectively, may include a plurality of s-shaped filaments 105 configured to connect certain forward peaks and reverse peaks. The cell patterns 66d, 66e, 66j, 66k of FIGS. 6D, 6E, 6J, and 6K, respectively, further include straight filaments 109 configured to connect certain forward peaks and reverse peaks. The cell patterns 66h, 66i of FIGS. 6H and 6I, respectively, further illustrate c-shaped filaments 110 configured to connect certain forward peaks and reverse peaks. As will be appreciated, the curved connection filaments 105, 110 exhibiting an s-shape or c-shape curvature may be more flexible than the straight filaments 109, but may be prone to twisting during compaction. The straight filaments 109, on the other hand, may be easier to compress but less flexible than the curved connection filaments 105, 110. Accordingly, the straight filaments 109 may be more acceptable for hybrid cell designs already having suitable flexibility.

FIGS. 6D, 6E, and 6L illustrate cell patterns 66d, 66e, 66l, respectively, having tip-to-tip connections between forward and reverse peaks. Such a configuration may provide a smaller compaction profile for the device 53. FIGS. 6F, 6G, 6H, and 6I illustrate cell patterns 66f, 66g, 66h, 66i having at least partially offset tip-to-tip connections between forward and reverse peaks. Such a configuration may provide increased flexibility and/or may increase vessel conformance.

FIGS. 6D, 6E, 6H, 6I, and 6J illustrate cell patterns 66d, 66e, 66h, 66i, 66j, respectively, having tip-to-tip connections between forward and reverse peaks of unit cells. Such a configuration may provide an easier compaction profile. FIGS. 6F and 6G illustrate cell patterns 66f, 66g, respectively, having valley-to-tip connections between forward and reverse peaks of unit cells. Such a configuration may provide increased flexibility for the device 53.

It will be appreciated that the various cell patterns described herein can be repeated (e.g., repetition of rows of unit cells), adjusted (e.g., different angles, different lengths, different thicknesses, etc.), and/or combined (e.g., permutations of any of the features disclosed herein) based on the desired properties of the device 53 or other vascular devices in which the patterns(s) are employed. In some embodiments, radiopaque markers may be integrated into a portion (e.g., the distal peaks of the forward free-peaks, around the filaments, etc.) of the device 53 so that a user (e.g., a physician) is able to actively monitor placement of the device 53. It will further be appreciated that both the first section 55 and the protruding section 57 may be formed by any of the patterns described herein, or any combination thereof. During the manufacturing or forming process for the device 53, the section of the device 53 that is to become the protruding section 57 may undergo heat treatment configured to shape set the pregnant portion 54 into the bulged configurations as generally described herein.

In one or more embodiments, FIGS. 6A-6L illustrate exemplary embodiments of at least a portion of the vascular device 53 at a stage of an exemplary manufacturing process that includes cutting and shaping a metallic sheet. A laser or electrochemical etching may cut out portions of the sheet, leaving a plurality of filaments, such as the filaments 59a, 59b described above with reference to FIG. 1A. In some embodiments, the first section 55 and the protruding section 57 may be integrally formed from the metallic sheet and otherwise not cut away from each other or separated. In embodiments in which both sections of the device are integrally fabricated by being cut from the same tube or sheet, the device may be characterized as a single-piece construction. The cut may be defined by features such as a thickness of the filaments, number of filaments, configuration and/or pattern of the filaments, etc.

The physical properties of the device 53 may be uniform throughout the device 53, or may vary depending on location or application. For example, filaments in a portion of the protruding section 57 may be thicker or higher in quantity than filaments in other portions of the device 53. Dimensions may be selected, for example, to accommodate certain vasculature, for flexibility, for wall conformance, etc.

After cutting or chemical etching, the sheet may be reshaped, such as into the shape of a tube or tubular, and the device 53 may be heat treated to shape set the first section 55 and the protruding section 57. The shape setting process may include successively shaping the sheet using an appropriate tooling (e.g., a mandrel) to stretch and confine the cut sheet into a new shape during the heat treatment. At the end of each heat treatment step, the cut sheet assumes the shape to which it was confined during the heat treatment process.

After shape setting the device 53, the protruding section 57 may be shaped further such that it is capable of transitioning into the further expanded configuration. For example, the device 53 may be further heat treated to impart further shape setting (e.g., extruding the sheet or tube or otherwise causing it to bulge outwardly) to at least the protruding section 57. The final shape and size of the protruding section 57 (e.g., the desired shape of the further expanded configuration) may obtained by repeating this process several times.

In order to obtain the final tubular shape of the device 53, opposite sides of the sheet may be required to be joined at the edges. In some embodiments, the edges may be welded, glued, adhered, mechanically crimped, mechanically swaged, braided, physical vapor deposited, chemical vapor deposited, or otherwise joined together to form a complete tubular profile. The various vascular implant devices described herein may also be formed using a cut metallic tube that is reshaped after being cut, although it will be appreciated that the properties of the initial tube and the pattern of the cut may be different.

In one or more embodiments, the first section 55 and the protruding section 57 may be integrally formed from the metallic tube or sheet and not cut away from each other. In embodiments in which both sections 55, 57 of the device 53 are integrally fabricated by being cut from the same tube or sheet, the device 53 may be characterized as a single-piece or monolithic construction. Single-piece construction may allow for easier manufacturing.

In other embodiments, however, some or all of the first section 55 and/or the protruding section 57 may be formed separately, and the separately formed portions may be coupled together by being welded, glued, adhered, mechanically crimped, mechanically swaged, braided, physical vapor deposited, chemical vapor deposited, combinations thereof, or the like. For example, the first separately formed portion may be cut from a tube or sheet and then be attached (e.g., welded, glued, adhered, mechanically crimped, mechanically swaged, braided, physical vapor deposited, chemical vapor deposited, etc.) to a pregnant portion cut from a separate tube of sheet. In such embodiments, the protruding section 57 may be made of a different material than the first section 55. In one or more embodiments, for example, the protruding section 57 may be made of platinum, platinum-iridium, or a polymer and the first section 55 may be made of nitinol or a CoCr alloy. Other combinations of materials are also possible, without departing from the scope of the disclosure. Separate or multi-piece construction may allow for independent selection of materials that are suited for the intended use.

Certain devices described herein may be advantageously used to treat aneurysms having a neck ratio (a ratio of fundus width to neck width) greater than about 2 to 1 and/or a neck width greater than about 4 mm. In treatment of such aneurysms, embolization coils may be prone to herniating into parent vessels because the size and/or shape of the aneurysm is not conducive to maintaining the coils in their inserted locus. In certain such embodiments, embolization coils are inserted in the fundus of the aneurysm after positioning a vascular device so that the embolization coils do not have an opportunity to herniate. It will be appreciated that certain devices described herein may also be used to treat aneurysms having a neck ratio less than about 2 to 1 and/or a neck width less than about 4 mm. In certain such embodiments, embolization coils may be inserted in the fundus of the aneurysm before positioning a vascular device.

Certain devices described herein may be advantageously used to treat aneurysms located off the efferent vessels or side branches of the bifurcation (e.g., having a neck substantially open to an efferent vessel). Devices traditionally used in treating aneurysms may have difficulty navigating to such locations and remaining anchored and stabilized at such locations. The embodiments of the device 53 disclosed herein, however, may overcome the difficulties encountered by those traditional devices. For example, the first section 55 may provide anchoring combined with the protruding section 57 which may provide scaffolding or reducing the effective neck size of the aneurysm.

"Occluding device" and "stent" are sometimes used herein interchangeably. In some embodiments, "cell" and "pore" as used herein are used interchangeably. In some embodiments, porosity refers to a value inversely proportional to lattice density.

The apparatus and methods discussed herein are not limited to the deployment and use of an occluding device within any particular vessels, but may include any number of different types of vessels. For example, in some aspects, vessels may include arteries or veins. In some aspects, the vessels may be suprathoracic vessels (e.g., vessels in the neck or above), intrathoracic vessels (e.g., vessels in the thorax), subthoracic vessels (e.g., vessels in the abdominal area or below), lateral thoracic vessels (e.g., vessels to the sides of the thorax such as vessels in the shoulder area and beyond), or other types of vessels and/or branches thereof.

In some aspects, the suprathoracic vessels may comprise at least one of intracranial vessels, cerebral arteries, and/or any branches thereof. For example, the suprathoracic vessels may comprise at least one of a common carotid artery, an internal carotid artery, an external carotid artery, a middle meningeal artery, superficial temporal arteries, an occipital artery, a lacrimal (ophthalmic) artery, an accessory meningeal artery, an anterior ethmoidal artery, a posterior ethmoidal artery, a maxillary artery, a posterior auricular artery, an ascending pharyngeal artery, a vertebral artery, a left middle meningeal artery, a posterior cerebral artery, a superior cerebellar artery, a basilar artery, a left internal acoustic (labyrinthine) artery, an anterior inferior cerebellar artery, a left ascending pharyngeal artery, a posterior inferior cerebellar artery, a deep cervical artery, a highest intercostal artery, a costocervical trunk, a subclavian artery, a middle cerebral artery, an anterior cerebral artery, an anterior communicating artery, an ophthalmic artery, a posterior communicating artery, a facial artery, a lingual artery, a superior laryngeal artery, a superior thyroid artery, an ascending cervical artery, an inferior thyroid artery, a thyrocervical trunk, an internal thoracic artery, and/or any branches thereof. The suprathoracic vessels may also comprise at least one of a medial orbitofrontal artery, a recurrent artery (of Heubner), medial and lateral lenticulostriate arteries, a lateral orbitofrontal artery, an ascending frontal (candelabra) artery, an anterior choroidal artery, pontine arteries, an internal acoustic (labyrinthine) artery, an anterior spinal artery, a posterior spinal artery, a posterior medial choroidal artery, a posterior lateral choroidal artery, and/or branches thereof. The suprathoracic vessels may also comprise at least one of perforating arteries, a hypothalamic artery, lenticulostriate arteries, a superior hypophyseal artery, an inferior hypophyseal artery, an anterior thalamostriate artery, a posterior thalamostriate artery, and/or branches thereof. The suprathoracic vessels may also comprise at least one of a precentral (pre-Rolandic) and central (Rolandic) arteries, anterior and posterior parietal arteries, an angular artery, temporal arteries (anterior, middle and posterior), a paracentral artery, a pericallosal artery, a callosomarginal artery, a frontopolar artery, a precuneal artery, a parietooccipital artery, a calcarine artery, an inferior vermian artery, and/or branches thereof.

In some aspects, the suprathoracic vessels may also comprise at least one of diploic veins, an emissary vein, a cerebral vein, a middle meningeal vein, superficial temporal veins, a frontal diploic vein, an anterior temporal diploic vein, a parietal emissary vein, a posterior temporal diploic vein, an occipital emissary vein, an occipital diploic vein, a mastoid emissary vein, a superior cerebral vein, efferent hypophyseal veins, infundibulum (pituitary stalk) and long hypophyseal portal veins, and/or branches thereof.

The intrathoracic vessels may comprise the aorta or branches thereof. For example, the intrathoracic vessels may comprise at least one of an ascending aorta, a descending aorta, an arch of the aorta, and/or branches thereof. The descending aorta may comprise at least one of a thoracic aorta, an abdominal aorta, and/or any branches thereof. The intrathoracic vessels may also comprise at least one of a subclavian artery, an internal thoracic artery, a pericardiacophrenic artery, a right pulmonary artery, a right coronary artery, a brachiocephalic trunk, a pulmonary trunk, a left pulmonary artery, an anterior interventricular artery, and/or branches thereof. The intrathoracic vessels may also comprise at least one of an inferior thyroid artery, a thyrocervical trunk, a vertebral artery, a right bronchial artery, a superior left bronchial artery, an inferior left bronchial artery, aortic esophageal arteries, and/or branches thereof.

In some aspects, the intrathoracic vessels may also comprise at least one of a right internal jugular vein, a right brachiocephalic vein, a subclavian vein, an internal thoracic vein, a pericardiacophrenic vein, a superior vena cava, a right superior pulmonary vein, a left brachiocephalic vein, a left internal jugular vein, a left superior pulmonary vein, an inferior thyroid vein, an external jugular vein, a vertebral vein, a right highest intercostal vein, a 6th right intercostal vein, an azygos vein, an inferior vena cava, a left highest intercostal vein, an accessory hemiazygos vein, a hemiazygos vein, and/or branches thereof.

In some aspects, the subthoracic vessels may comprise at least one of renal arteries, inferior phrenic arteries, a celiac trunk with common hepatic, left gastric and splenic arteries, superior suprarenal arteries, a middle suprarenal artery, an inferior suprarenal artery, a right renal artery, a subcostal artery, 1st to 4th right lumbar arteries, common iliac arteries, an iliolumbar artery, an internal iliac artery, lateral sacral arteries, an external iliac artery, a testicular (ovarian) artery, an ascending branch of deep circumclex iliac artery, a superficial circumflex iliac artery, an inferior epigastric artery, a superficial epigastric artery, a femoral artery, a ductus deferens and testicular artery, a superficial external pudendal artery, a deep external pudendal artery, and/or branches thereof. The subthoracic vessels may also comprise at least one of a superior mesenteric artery, a left renal artery, an abdominal aorta, an inferior mesenteric artery, colic arteries, sigmoid arteries, a superior rectal artery, 5th lumbar arteries, a middle sacral artery, a superior gluteal artery, umbilical and superior vesical arteries, an obturator artery, an inferior vesical and artery to ductus deferens, a middle rectal artery, an internal pudendal artery, an inferior gluteal artery, a cremasteric, pubic (obturator anastomotic) branches of inferior epigastric artery, a left colic artery, rectal arteries, and/or branches thereof.

In some aspects, the lateral thoracic vessels may comprise at least one of humeral arteries, a transverse cervical artery, a suprascapular artery, a dorsal scapular artery, and/or branches thereof. The lateral thoracic vessels may also comprise at least one of an anterior circumflex humeral artery, a posterior circumflex humeral artery, a subscapular artery, a circumflex scapular artery, a brachial artery, a thoracodorsal artery, a lateral thoracic artery, an inferior thyroid artery, a thyrocervical trunk, a subclavian artery, a superior thoracic artery, a thoracoacromial artery, and/or branches thereof.

In some embodiments, a catheter, such as that described in U.S. patent application Ser. No. 12/731,110, which was filed on Mar. 24, 2010 and which is incorporated herein by reference in its entirety, can be used to deliver an occluding device delivery system. The delivery system can include an expandable occluding device (e.g., stent) configured to be placed across an aneurysm that is delivered through the distal portion of the catheter, out a distal tip, and into the vasculature adjacent an aneurysm in, for example, the middle cerebral artery. A proximal portion of the catheter can remain partially or entirely within a guiding catheter during delivery, and an intermediate portion, taper portion, and distal portion of the catheter can extend distally of the guiding catheter. The occluding device can be released at the target location and can be used to occlude blood flow into the aneurysm. The catheter can be used to reach target locations (e.g., aneurysms) located elsewhere in the body as well, include but not limited to other arteries, branches, and blood vessels such as those described above.

In some embodiments, a method of implantation and monitoring can be used, for example, with the deployment systems described above. The method can include implanting an occluding device within the vasculature of a patient such that the device extends, within and along a vessel, past an aneurysm. Example occluding devices, deployment devices, microcatheters for delivery of occluding devices, and deployment methods are described in U.S. Provisional Application No. 60/574,429, filed on May 25, 2004; U.S. patent application Ser. No. 11/136,395 (U.S. Patent Application Publication No. 2005/0267568), filed on May 25, 2005; U.S. patent application Ser. No. 11/420,025 (U.S. Patent Application Publication No. 2006/0206200), filed on May 24, 2006; U.S. patent application Ser. No. 11/420,027 (U.S. Patent Application Publication No. 2006/0206201), filed on May 24, 2006; U.S. patent application Ser. No. 11/136,398 (U.S. Patent Application Publication No. 2006/0271149), filed on May 25, 2005; U.S. patent application Ser. No. 11/420,023 (U.S. Patent Application Publication No. 2006/0271153), filed on May 24, 2006; U.S. patent application Ser. No. 12/490,285 (U.S. Patent Application Publication No. 2009/0318947), filed on Jun. 23, 2010; U.S. patent application Ser. No. 12/425,604 (U.S. Patent Publication No. 2009/0287288), filed on Apr. 17, 2009; U.S. patent application Ser. No. 12/425,617 (U.S. Patent Application Publication No. 2009/0287241), filed on Apr. 17, 2009; U.S. patent application Ser. No. 12/431,716 (U.S. Patent Application Publication No. 2009/0270974), filed on Apr. 28, 2009; U.S. patent application Ser. No. 12/431,717, filed on Apr. 28, 2009; U.S. patent application Ser. No. 12/431,721 (U.S. Patent Publication No. 2009/0292348), filed on Apr. 28, 2009; U.S. patent application Ser. No. 12/490,285 (U.S. Patent Application Publication No. 2010/0010624), filed on Jun. 23, 2009; U.S. patent application Ser. No. 12/490,285 (U.S. Patent Publication No. 2009/0319017), filed on Jun. 23, 2009; U.S. patent application Ser. No. 12/731,110, filed on Mar. 24, 2010; and U.S. patent application Ser. No. 12/751,997, filed on Mar. 31, 2010; each of which is incorporated herein by reference in its entirety. Other occluding devices, deployment devices, catheters, and deployment methods are also possible.

In some embodiments, the method includes monitoring the aneurysm post-operatively to confirm occlusion of the aneurysm. In some embodiments, a doctor or other provider may determine that an occluding device, after implantation, is operating correctly based on observation that full or partial occlusion of the aneurysm has occurred, for example using the observation and/or determination techniques described herein.

According to certain embodiments, observation of at least partial occlusion of the aneurysm immediately after implantation of the occluding device provides an indication that the occluding device is operating correctly. As a result, prolonged monitoring of the patient after implantation of the occluding device may not be necessary. In some embodiments, monitoring the aneurysm can include imaging the aneurysm through known imaging techniques to confirm that the aneurysm is completely or at least partially occluded. For example, imaging techniques such as those utilizing fluoroscopy, CAT scans, X-rays, MRIs, or other suitable imaging techniques may be used to monitor the aneurysm.

In some embodiments, two-dimensional imaging is utilized to monitor the aneurysm during and/or after delivery of the device within the vessel. In some embodiments, three-dimensional imaging is utilized to monitor the aneurysm. For example, imaging of the delivery can be monitored during advancement of the device in the vasculature, deployment of the device at the aneurysm, and after deployment of the device prior to initiation of withdrawal of the delivery system. In some embodiments, contrast agent can be delivered during advancement of the device in the vasculature, deployment of the device at the aneurysm, and/or after deployment of the device prior to initiation of withdrawal of the delivery system. The contrast agent can be delivered through the same catheter used to deliver the occluding device, or through another catheter or device commonly used to delivery contrast agent. For example, the catheter may comprise a lumen extending from a position outside the patient to a position proximate to the site to be treated (e.g., via a Y-joint in a handle of the catheter), and the lumen can be used to deliver contrast agent, drugs, saline, etc. In certain such embodiments, the lumen may be coaxial with the delivery lumen, side-by-side the delivery lumen, etc. In some embodiments, initiation of withdrawal of the delivery system can be based on results from imaging the device and aneurysm following expansion of the device at the aneurysm. In some embodiments, the results obtained from the imaging include partial occlusion of the aneurysm, which results then provide indication that the device is promoting occlusion of the aneurysm.

Although rare, in some instances, occlusion may not occur with the deployment of a single occluding device. In certain such instances, monitoring of the aneurysm and device following deployment of the occluding device at the aneurysm can indicate whether partial occlusion is occurring. If partial occlusion does not occur, some embodiments provide for deployment of a second device within the first device to further promote occlusion within the aneurysm. Regardless of whether one or multiple devices are deployed, upon confirmation that partial occlusion is occurring within the aneurysm, withdrawal of the delivery system can be initiated.

In some embodiments, other techniques may be used to determine whether at least partial occlusion of the aneurysm has occurred. For example, blood flow into an aneurysm may be monitored after positioning of the device within the vessel to determine whether occlusion is occurring. Reduced blood flow into an aneurysm may be an indication that occlusion of the aneurysm is occurring. In some embodiments, radio-opaque markers or other suitable trackers may be used to enable or enhance the monitoring of the blood flow into an aneurysm. In some embodiments, the pressure of the blood flow into an aneurysm, or the pressure exerted on the walls of the aneurysm may be monitored to determine if occlusion of the aneurysm is occurring. For example, reduced outward pressure being exerted on the walls of the aneurysm, as determined from blood flow patterns in the vessel distal the aneurysm measured by an endovascular transducer, may indicate that at least partial occlusion is occurring. In some embodiments, the stiffness or the hardness of the aneurysm may be measured to determine whether occlusion is occurring. For example, occlusion of the aneurysm may occur, leading to at least partial thrombosis within the aneurysm. As a result, the aneurysm may be stiffer or harder, as determined by observing variance in pulsation, than it would have been had occlusion not occurred.

The apparatus and methods discussed herein are not limited to the deployment and use of an occluding device or stent within the vascular system but may include any number of further treatment applications. Other treatment sites may include areas or regions of the body such as organ bodies. Modification of each of the above-described apparatus and methods for carrying out the subject technology, and variations of aspects of the disclosure that are apparent to those of skill in the art are intended to be within the scope of the claims. Furthermore, no element, component or method step is intended to be dedicated to the public regardless of whether the element, component or method step is explicitly recited in the claims.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations which will be apparent to those skilled in the art may be made in the arrangement, operation and details of the method and apparatus of the subject technology disclosed herein without departing from the spirit and scope of the subject technology as defined in the appended claims. Therefore, the scope of the subject technology should be determined by the appended claims and their legal equivalents. Furthermore, no element, component or method step is intended to be dedicated to the public regardless of whether the element, component or method step is explicitly recited in the claims. Underlined and/or italicized headings and subheadings are used for convenience only, do not limit the subject technology, and are not referred to in connection with the interpretation of the description of the subject technology. In the claims and description, unless otherwise expressed, reference to an element in the singular is not intended to mean "one and only one" unless explicitly stated, but rather is meant to mean "one or more." In addition, it is not necessary for a device or method to address every problem that is solvable by different embodiments of the disclosure in order to be encompassed by the claims.

What is claimed is:

1. A vascular stent, comprising:
   a proximal section having a first cross-sectional dimension and being configured to anchor in an afferent vessel of a bifurcation proximate to an aneurysm, the proximal section comprising a tubular shape that defines a proximal lumen;
   a distal section having a second cross-sectional dimension and being configured to be positioned in an efferent vessel of the bifurcation, the distal section comprising a tubular shape that defines a distal lumen; and
   a protruding section, between the proximal and distal sections, having a third cross-sectional dimension, the protruding section (i) being configured to abut an ostium of the aneurysm when the protruding section is positioned at the bifurcation, (ii) defining an intermediate lumen in fluid communication with the proximal and distal lumens, and (iii) having a strut pattern that is substantially the same as strut patterns of the proximal and distal sections;
   wherein the proximal, distal and protruding sections are expandable from a compressed configuration to an expanded configuration;
   wherein, in the compressed configuration, first cells of the proximal section and/or the distal section have a first compressed cell size greater than a second compressed cell size of second cells of the protruding section;
   wherein, in the expanded configuration, the first cells have a first expanded cell size substantially equal to a second expanded cell size of the second cells.

2. The stent of claim 1, wherein the protruding section is configured to inhibit dislodgment of objects out of the aneurysm.

3. The stent of claim 1, wherein filaments of the protruding section terminate in free peaks at a region between the protruding section and the proximal section.

4. The stent of claim 1, wherein cell sizes of the strut pattern in the protruding section are configured to allow perfusion of fluid to efferent vessels.

5. The stent of claim 1, wherein the proximal, distal, and protruding sections comprise nonuniform cross-sectional dimensions when the stent is unconstrained.

6. The stent of claim 1, wherein the protruding section comprises an irregular-shaped cross-section.

7. The stent of claim 1, wherein the protruding section is expandable to a further expanded configuration, the further expanded configuration defining a fourth cross-sectional dimension greater than the third cross-sectional dimension.

8. The stent of claim 1, wherein the proximal, distal, and protruding sections comprise woven filaments.

9. The stent of claim 1, wherein at least one of the proximal, distal, and protruding sections is self-expandable.

10. The stent of claim 1, wherein at least one of the proximal and distal sections comprises a first material and the protruding section comprises a second material different from the first material.

11. The stent of claim 1, further comprising (i) a first intermediate section, between the proximal and protruding sections, having a first taper, from the proximal section to the protruding section, and (ii) a second intermediate section, between the distal and protruding sections, having a second taper, from the distal section to the protruding section, the first taper having a different degree of tapering than the second taper.

12. The stent of claim 11, wherein the second taper has a steeper degree of tapering than does the first taper.

13. The stent of claim 1, wherein the protruding section bulges radially outward along substantially an entire circumference of the device.

14. The stent of claim 1, wherein a bulge of the protruding section provides a generally asymmetrical profile.

15. The stent of claim 1, wherein at least a portion of the protruding section comprises a lower filament density than at least one of another portion of the protruding section, the proximal section, and the distal section.

* * * * *